United States Patent [19]

Gunther et al.

[11] Patent Number: 4,607,000

[45] Date of Patent: Aug. 19, 1986

[54] AMIDO SUBSTITUTED DIVALENT CHALCOGENIDE FOG INHIBITING AGENTS FOR SILVER HALIDE PHOTOGRAPHY

[75] Inventors: Wolfgang H. H. Gunther, Webster; Roger Lok, Hilton, both of N.Y.

[73] Assignee: Eastman Kodak Company, Rochester, N.Y.

[21] Appl. No.: 719,838

[22] Filed: Apr. 4, 1985

[51] Int. Cl.[4] .................................................. G03C 1/34
[52] U.S. Cl. ..................................... 430/428; 430/447; 430/448; 430/612; 430/607; 430/570; 430/599; 430/611; 260/550
[58] Field of Search ............... 430/607, 603, 612, 428, 430/429, 447, 448, 570, 599, 611; 260/550

[56] References Cited

U.S. PATENT DOCUMENTS 3,397,986  8/1968  Millikan et al. ..................... 430/611

FOREIGN PATENT DOCUMENTS 57817  5/1978  Japan .................................. 430/603
1282303  7/1972  United Kingdom ................ 430/612

OTHER PUBLICATIONS

*Research Disclosure*, vol. 176, Dec. 1978, Item 17643.
Ludwig Reichel and Ernst Kirschbaum, Uber Aromatische Tellurverbindungen (I. Mitteilung uber Organometallverbindungen) *Analen der Chemie*, vol. 523, 1936, pp. 211–221.
Cobbledick et al "Some New Organotellurium Compounds Derived from Azobenzene: The Crystal and Molecular Structure of (2-Penylazophenyl-C,N')-Tellurium(II) Chloride", *Journal of Chemical Research*, pp. 1901–1924, 1979.
Mbuyi et al, The 1,3-Benzotellurazole: A New Heterocyclic System, *Tetrahedron Letters*, vol. 24, No. 52, pp. 5873–5876, 1983.

*Primary Examiner*—Won H. Louie
*Attorney, Agent, or Firm*—Carl O. Thomas

[57] ABSTRACT

Radiation sensitive silver halide photographic elements are disclosed which are protected from fog by amido substituted aromatic tellurochalcogenides. The amido substituted aromatic tellurochalcogenides can be initially incorporated in the photographic element as manufactured or during processing.

15 Claims, No Drawings

AMIDO SUBSTITUTED DIVALENT CHALCOGENIDE FOG INHIBITING AGENTS FOR SILVER HALIDE PHOTOGRAPHY

FIELD OF THE INVENTION

This invention relates to photography. It relates to silver halide photographic elements and to imaging processes.

BACKGROUND OF THE INVENTION

In the course of processing a photographic element containing an imagewise exposed silver halide emulsion layer reduced silver can be formed either as a direct or inverse function of exposure. At the same time, at least a low level of reduced silver formation also occurs independently of imagewise exposure. The term "fog" is herein employed to indicate the density of the processed photographic element attributable to the latter, usually measured in minimum density areas. In color photography fog is typically observed as image dye density rather than directly as silver density.

Over the years a variety of differing materials have been introduced into silver halide emulsions to inhibit the formation of fog. *Research Disclosure*, Vol. 176, December 1978, Item 17643, Section VI, lists the more commonly employed fog inhibiting agents. *Research Disclosure* is published by Kenneth Mason Publications, Ltd., The Old Harbourmaster's, 8 North Street, Emsworth, Hampshire PO10 7DD, England.

It is known to employ as fog inhibiting agents compounds having two aromatic nuclei linked by two divalent sulfur atoms and analogous compounds in which one or both of the sulfur atoms are replaced by selenium atoms. Exemplary of such fog inhibiting agents are bis(p-aminophenyl)disulfides disclosed by Millikan et al U.S. Pat. No. 3,397,986.

Asahi Japanese Kokai No. 57817/78, laid open May 25, 1978, discloses the use of a variety of tellurium compounds as chemical sensitizers for silver halide emulsions. In one of a variety of differing forms the tellurium compounds can satisfy the formula

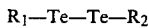

wherein $R_1$ and $R_2$ are organic groups, such as substituted or unsubstituted alkyl or aryl groups or carbonyl containing organic groups. Aryl substituents disclosed are methyl, ethyl, methoxy, amino, dimethylamino, hydroxy, and halogen.

Lok et al U.S. Ser. No. 719,839, filed Apr. 4, 1985 concurrently herewith, titled DIVALENT CHALCOGENIDE FOG INHIBITING AGENTS FOR SILVER HALIDE PHOTOGRAPHY, commonly assigned, discloses aromatic tellurochalcogenides to be useful silver halide fog inhibiting agents.

Ludwig Reichel and Ernst Kirschbaum, Uber Aromatsiche Tellurverbindungen (I. Mitteilung uber Organometallverbindungen), *Analen der Chemie*, Vol. 523, 1936, pp. 211–221, describes the preparation of bis(4-acetamidophenyl)ditelluride.

Cobbledick et al, "Some New Organotellurium Compounds Derived from Azobenzene: The Crystal and Molecular Structure of (2-Phenylazophenyl-C,N')tellurium(II) Chloride", *Journal of Chemical Research*, pp. 1901–1924, 1979, discloses 2,2'-ditellurobisbenzenamine.

SUMMARY OF THE INVENTION

In one aspect this invention is directed to a photographic element containing a radiation sensitive silver halide emulsion and an effective amount of a fog inhibiting agent comprised of a divalent tellurium atom directly linked to a first aromatic nucleus and linked to a second aromatic nucleus through at least one divalent middle chalcogen atom characterized in that said first aromatic nucleus includes an amido ring sustituent.

In another aspect this invention is directed to a method of producing a photographic image comprising processing a photographic element containing at least one imagewise exposed silver halide emulsion in the presence of a fog inhibiting agent comprised of a divalent tellurium atom directly linked to a first aromatic nucleus and linked to a second aromatic nucleus through at least one divalent middle chalcogen atom characterized in that said first aromatic nucleus includes an amido ring sustituent.

In an additional aspect this invention is directed to a novel compound having a divalent tellurium atom directly linking a first aromatic nucleus and a second aromatic nucleus through at least one divalent middle chalcogen atom, the first aromatic nucleus including an amido ring sustituent which is characterized in being positioned ortho to said divalent tellurium linking atom.

The present invention permits the use of photographic elements containing radiation sensitive silver halide emulsions to produce photographic images exhibiting low levels of fog. Further, the invention permits a speed/fog relationship to be realized that is superior to that of known fog inhibiting agents closely related in structural form. The invention affords an alternative and generally superior approach to fog inhibition that allows fog inhibiting agent concentrations to be reduced as compared to aromatic diselenide and aromatic disulfide fog inhibiting agents by approximately an order of magnitude.

The invention also makes available a novel class of amido substituted tellurochalcogenides, procedures for the preparation of which have not heretofore been known.

DESCRIPTION OF PREFERRED EMBODIMENTS

Compounds employed in the practice of the present invention have two aromatic nuclei linked by two or more divalent middle chalcogen atoms, one of which is a divalent tellurium atom linked directly to one of the aromatic nuclei. Such compounds are hereinafter more succinctly referred to as aromatic tellurochalcogenides. In a preferred form, in which the aromatic nuclei are linked by two divalent tellurium atoms, the compounds are hereinafter referred to as aromatic ditellurides. Middle chalcogen atoms are sulfur, selenium, and tellurium.

The aromatic tellurochalcogenides employed in the practice of the present invention contain a divalent tellurium atom linked to a first aromatic nucleus which is ring substituted with an amido group. Although the amido group can be positioned in any synthetically convenient ring position, superior properties are observed when the amido group is positioned ortho to the divalent tellurium atom.

The fog inhibiting agents employed in the practice of this invention include those represented by the formula:

  (I)

wherein
- Ar is an amido substituted first aromatic nucleus;
- Ar' is a second aromatic nucleus; and
- Ch is one or more middle chalogen atoms.

Since it is believed that in use cleavage of the chalcogen to chalcogen bond occurs to produce Ar—Te and Ar'—Ch moieties that inhibit fog formation, the presence of more than two middle chalcogen atoms in the linking group is not necessary. Thus, the preferred compounds are those in which Ch is a single middle chalcogen atom.

Specifically preferred compounds for the practice of this invention are aromatic ditellurides satisfying the formula:

$$Ar\text{—}Te\text{—}Te\text{—}Ar' \qquad (II)$$

wherein
Ar and Ar' are amido substituted aromatic nuclei.

The amido substituent can take the form of any synthetically convenient amido group. In a preferred form the amido substituent can satisfy the formula:

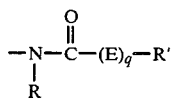

$$-\underset{R}{\underset{|}{N}}-\overset{O}{\overset{\|}{C}}-(E)_q-R' \qquad (III)$$

wherein
- E is a divalent oxy, thio, or amino linking group;
- R can be chosen from the group consisting of hydrogen and an optionally substituted aliphatic hydrocarbon group;
- R' can be chosen from the group consisting of hydrogen and an optionally substituted aliphatic or aromatic hydrocarbon group; and
- q is 0 or 1.

Superior performance has been observed when R is an optionally substituted aliphatic hydrocarbon as opposed to hydrogen. However, in every instance superior performance has been observed as compared to aromatic tellurochalcogenides which are not ring substituted or contain another ring substituent, such as a methoxy or amino substituent, as demonstrated in the examples below.

Aliphatic hydrocarbon moieties forming the aliphatic hydrocarbon substituents R and R' as well as optional aliphatic hydrocarbon substituents of Ar and Ar' can be chosen from among alkyl, alkenyl, and alkynyl groups. The aliphatic hydrocarbon moieties can contain any convenient number of carbon atoms, but preferably contain from 1 to 10 carbon atoms. Preferred aliphatic hydrocarbon substituents are lower alkyl substituents of from 1 to 6 carbon atoms.

The aromatic hydrocarbon moieties forming the aromatic nuclei Ar and Ar' and the aromatic hydrocarbon substituent R' preferably contain from 6 to 14 ring carbon atoms and are most preferably phenyl or naphthyl moieties.

The aliphatic hydrocarbon substituents R and R' can be optionally substituted with aromatic moieties to form aralkyl groups, and the aromatic moieties forming R', Ar, and Ar' can be optionally substituted with aliphatic hydrocarbon moieties. These hydrocarbon moieties can, if desired, be linked through a divalent oxygen or sulfur atom—that is, they can take form of oxy or thio groups. Other contemplated substituents of R, R', Ar, and Ar' include halogen atoms and cyano, amino, amido, sulfonamido, sulfamoyl, ureido, thioureido, hydroxy, —C(O)M, or —S(O)$_2$M, wherein M is chosen to complete an aldehyde, ketone, acid, ester, thioester, amide, or salt.

R and R' in specifically preferred forms of the invention are independently chosen from among a lower alkyl group, such a methyl, ethyl, propyl, butyl, or hexyl group; an alkenyl group, such as a vinyl or allyl group; or an alkynyl group, such as a propargyl or 2-butynyl group. Any one of these groups, but most typically the lower alkyl groups, can be substituted with an oxy, thio, sulfo, sulfonyl, sulfato, halo, or carboxy substituent.

When q in formula (III) is 1, the amido substituent can be presented as —N(R)C(O)ER'. That is, the amido substituent can be an oxyamido, thioamido, or ureido substituent. In a specifically preferred form q is zero, and the amido substituent is represented as —N(R)-C(O)R'.

Ar and Ar' in specifically preferred forms of the invention are phenyl or naphthyl nuclei which are each ring substituted with an amido group satisfying formula (III). The naphthyl nuclei can be either $\alpha$ or $\beta$ naphthyl nuclei, referenced to the middle chalogen atom. Ortho and para amido substituted phenyl nuclei are preferred, with ortho amido substituted phenyl nuclei showing the highest levels of fog inhibiting activity. The phenyl or naphthyl nuclei are preferably free of substituents other than the middle chalcogen atom and the amido group, but can be optionally additionally ring substituted with one or more substituents chosen from among aliphatic or aromatic hydrocarbon moieties optionally linked through a divalent oxygen or sulfur atom, halogen atoms, cyano groups, amino groups, sulfonamido groups, sulfamoyl groups, thioureido groups, hydroxy groups, —C(O)M groups, and —S(O)$_2$M groups, wherein M is chosen to complete an acid, thioester, or salt.

The aromatic tellurochalcogenide fog inhibiting agents are preferably incorporated in the photographic element to be protected prior to exposure and processing—e.g., at the time of manufacture. When the aromatic tellurochalcogenide is being relied upon to reduce fog the origin of which antedates processing, it is essential that the aromatic tellurochalcogenide be incorporated in the silver halide emulsion layer or layers to be protected. It is generally most convenient to introduce the aromatic tellurochalcogenide into the silver halide emulsion after chemical ripening of the emulsion and before coating.

When the aromatic tellurochalcogenide is intended to become active at the time of processing, it can be incorporated within the photographic element at any location which permits permeation of one or more silver halide emulsion layers being imagewise developed. For example, the aromatic tellurochalcogenide can be located in one or more silver halide emulsion layers or other hydrophilic colloid layers, such as in an overcoat, interlayer, or subbing layer. When the aromatic tellurochalcogenide is intended to become active at the time of processing, it is generally most convenient to add the aromatic tellurochalcogenide as a component of a processing solution, such as predevelopment bath or a developer, allowing it to permeate the silver halide emulsion layer or layers prior to or during development.

Any amount of aromatic tellurochalcogenide effective to reduce fog can be employed. Optimum amounts of fog inhibiting agents for specific applications are usually determined empirically by varying concentrations. Such investigations are typically relied upon to identify optimum fog inhibiting concentrations or other effects, such as reduction in photographic speed. Based on the investigations reported below, when the aromatic tellurochalcogenide is incorporated in a silver halide emulsion prior to coating, concentrations of from about 1.0 to 0.005 millimole per silver mole, preferably 0.5 to 0.01 millimole per silver mole, and optimally from 0.15 to 0.015 millimole per silver mole, are contemplated. When the aromatic tellurochalcogenide is incorporated in a processing solution, concentration ranges from minimum effective amounts—e.g., typically at least 0.05 millimole per liter—up to about 0.5 millimole per liter are contemplated.

It is, of course, recognized that conventional fog inhibiting agents, such as those illustrated by *Research Disclosure*, Item 17643, Section VI, cited above, can be employed in combination with aromatic tellurochalcogenide in the practice of this invention. Since it is recognized that fog inhibiting agents operate by a variety of differing mechanisms, the effects produced by combinations of aromatic tellurochalcogenide and conventional fog inhibiting agents will range from highly interdependent to independently additive, but in any case optimum concentrations are susceptible to empirical determination.

In addition to the fog inhibiting agent this invention additionally requires a photographic element containing a radiation sensitive silver halide emulsion. These silver halide emulsions can be comprised of silver bromide, silver chloride, silver iodide, silver chlorobromide, silver chloroiodide, silver bromoiodide, silver chlorobromoiodide or mixtures thereof. The emulsions can include silver halide grains of any conventional shape or size. Specifically, the emulsions can include coarse, medium or fine silver halide grains of either regular (e.g., cubic or octahedral) or irregular (e.g., multiply twinned or tabular) crystallographic form. Recently developed high aspect ratio tabular grain emulsions, such as those disclosed by Wilgus et al U.S. Pat. No. 4,434,226, Daubendiek et al U.S. Pat. No. 4,414,310, Wey U.S. Pat. No. 4,399,215, Solberg et al U.S. Pat. No. 4,433,048, Mignot U.S. Pat. No. 4,386,156, Evans et al U.S. Pat. No. 4,504,570, Maskasky U.S. Pat. No. 4,400,463, Wey et al U.S. Pat. No. 4,414,306, and Maskasky U.S. Pat. No. 4,435,501, are specifically contemplated. Sensitizing compounds, such as compounds of copper, thallium, lead, bismuth, cadmium and Group VIII noble metals, can be present during precipitation of the silver halide emulsion, as illustrated by Arnold et al U.S. Pat. No. 1,195,432, Hochstetter U.S. Pat. No. 1,951,933, Trivelli et al U.S. Pat. No. 2,448,060, Overman U.S. Pat. No. 2,628,167, Mueller et al U.S. Pat. No. 2,950,972, Sidebotham U.S. Pat. No. 3,488,709 and Rosecrants et al U.S. Pat. No. 3,737,313.

The silver halide emulsions can be either monodisperse or polydisperse as precipitated. The grain size distribution of the emulsions can be controlled by silver halide grain separation techniques or by blending silver halide emulsions of differing grain sizes. The emulsions can include Lippmann emulsions and ammoniacal emulsions, as illustrated by Glafkides, *Photographic Chemistry*, Vol.1, Fountain Press, London, 1958, pp.365-368 and pp.301-304; excess halide ion ripened emulsions as described by G. F. Duffin, *Photographic Emulsion Chemistry*, Focal Press Ltd., London, 1966, pp.60-72; thiocyanate ripened emulsions, as illustrated by Illingsworth U.S. Pat. No. 3,320,069; thioether ripened emulsions, as illustrated by McBride U.S. Pat. No. 3,271,157, Jones U.S. Pat. No. 3,574,628 and Rosecrants et al U.S. Pat. No. 3,737,313 or emulsions containing weak silver halide solvents, such as ammonium salts, as illustrated by Perignon U.S. Pat. No. 3,784,381 and *Research Disclosure*, Vol.134, June 1975, Item 13452.

The emulsions can be surface-sensitive emulsions—i.e., emulsions that form latent images primarily on the surfaces of the silver halide grains—or internal latent image-forming emulsions—i.e., emulsions that form latent images predominantly in the interior of the silver halide grains, as illustrated by Knott et al U.S. Pat. No. 2,456,953, Davey et al U.S. Pat. No. 2,592,250, Porter et al U.S. Pat. Nos. 3,206,313 and 3,317,322, Bacon et al U.S. Pat. No. 3,447,927, Evans U.S. Pat. No. 3,761,276, Morgan U.S. Pat. No. 3,917,485, Gilman et al U.S. Pat. No. 3,979,213, Miller U.S. Pat. No. 3,767,413, and Evans et al U.S. Pat. No. 4,504,570.

The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent, as illustrated by Ives U.S. Pat. No. 2,563,785, Evans U.S. Pat. No. 3,761,276, Knott et al U.S. Pat. No. 2,456,953, Jouy U.S. Pat. No. 3,511,662, and Evans et al U.S. Pat. No. 4,504,570.

Blends of surface sensitive emulsions and internally fogged, internal latent image-forming emulsions can be employed, as illustrated by Luckey et al U.S. Pat. Nos. 2,996,382, 3,397,987 and 3,705,858, Luckey U.S. Pat. No. 3,695,881, *Research Disclosure*, Vol.134, June 1975, Item 13452, Millikan et al Defensive Publication T-904017, Apr. 21, 1972 and Kurz *Research Disclosure*, Vol.122, June 1974, Item 12233.

The aromatic tellurochalcogenide compounds are preferably employed to reduce fog in negative working silver halide emulsions and most preferably those that contain silver halide grains which form surface latent images on exposure.

The silver halide emulsions can be surface sensitized. Noble metal (e.g., gold), middle chalcogen (e.g., sulfur, selenium, or tellurium), and reduction sensitizers, employed individually or in combination are specifically contemplated. Typical chemical sensitizers are listed in *Research Disclosure*, Item 17643, cited above, Section III.

The silver halide emulsions can be spectrally sensitized with dyes from a variety of classes, including the polymethine dye class, which includes the cyanines, merocyanines, complex cyanines and merocyanines (i.e., tri-, tetra-, and poly-nuclear cyanines and merocyanines), oxonols, hemioxonols, styryls, merostyryls, and streptocyanines. Illustrative spectral sensitizing dyes are disclosed in *Research Disclosure*, Item 17643, cited above, Section IV.

The silver halide emulsions as well as other layers of the photographic elements of this invention can contain as vehicles hydrophilic colloids, employed alone or in combination with other polymeric materials (e.g., latices). Suitable hydrophilic materials include both naturally occurring substances such as proteins, protein derivatives, cellulose derivatives—e.g., cellulose esters, gelatin—e.g., alkali treated gelatin (cattle, bone, or hide gelatin) or acid treated gelation (pigskin gelatin), gelatin derivatives—e.g., acetylated gelatin, phthalated gelatin, and the like, polysaccharides such as dextran, gum arabic, zein, casein, pectin, collagen derivatives, collodion, agar-agar, arrowroot, and albumin. The vehicles can be hardened by conventional procedures. Further details of the vehicles and hardeners are provided in *Research Disclosure,* Item 17643, cited above, Sections IX and X.

The silver halide photographic elements of this invention can contain other addenda conventional in the photographic art. Useful addenda are described, for example, in *Research Disclosure,* Item 17643, cited above. Other conventional useful addenda include desensitizers, couplers (such as dye forming couplers, masking couplers and DIR couplers) DIR compounds, anti-stain agents, image dye stabilizers, absorbing materials such as filter dyes and UV absorbers, light scattering materials, antistatic agents, coating aids, plasticizers and lubricants, and the like.

The photographic elements of the present invention can be simple black-and-white or monochrome elements comprising a support bearing a layer of the silver halide emulsion, or they can be multilayer and/or multicolor elements. The photographic elements produce images ranging from low contrast to very high contrast, such as those employed for producing half tone images in graphic arts. They can be designed for processing with separate solutions or for in-camera processing. In the latter instance the photographic elements can include conventional image transfer features, such as those illustrated by *Research Disclosure,* Item 17643, cited above, Section XXIII. Multicolor elements contain dye image forming units sensitive to each of the three primary regions of the spectrum. Each unit can be comprised of a single emulsion layer or of multiple emulsion layers sensitive to a given region of the spectrum. The layers of the element, including the layers of the image forming units, can be arranged in various orders as known in the art. In an alternative format, the emulsion or emulsions can be disposed as one or more segmented layers, e.g., as by the use of microvessels or microcells, as described in Whitmore U.S. Pat. No. 4,387,154.

A preferred color photographic element according to this invention comprises a support bearing at least one blue sensitive silver halide emulsion layer having associated therewith a yellow dye forming coupler, at least one green sensitive silver halide emulsion layer having associated therewith a magenta dye forming coupler and at least one red sensitive silver halide emulsion layer having associated therewith a cyan dye forming coupler, at least one of the silver halide emulsion layers containing an aromatic tellurochalcogenide fog inhibiting compound.

The elements of the present invention can contain additional layers conventional in photographic elements, such as overcoat layers, spacer layers, filter layers, antihalation layers, scavenger layers and the like. The support can be any suitable support used with photographic elements. Typical supports include polymeric films, paper (including polymer-coated paper), glass and the like. Details regarding supports and other layers of the photographic elements of this invention are contained in *Research Disclosure,* Item 17643, cited above, Section XVII.

The photographic elements can be imagewise exposed with various forms of energy, which encompass the ultraviolet, visible, and infrared regions of the electromagnetic spectrum as well as electron beam and beta radiation, gamma ray, X ray, alpha particle, neutron radiation, and other forms of corpuscular and wave-like radiant energy in either noncoherent (random phase) forms or coherent (in phase) forms, as produced by lasers. When the photographic elements are intended to be exposed by X rays, they can include features found in conventional radiographic elements, such as those illustrated by *Research Disclosure,* Vol. 184, August 1979, Item 18431.

Processing of the imagewise exposed photographic elements in the presence of the aromatic tellurochalcogenide need not otherwise differ from conventional processing. Processing procedures, developing agents, and development modifiers are illustrated by *Research Disclosure,* Item 17643, cited above, Sections XIX, XX, and XXI, respectively. In its preferred application the invention relates to silver halide photographic elements which are processed in aqueous alkaline developers in the presence of the aromatic tellurochalcogenide.

PREPARATION OF AMIDO SUBSTITUTED AROMATIC TELLUROCHALCOGENIDES

Ludwig Reichel and Ernst Kirschbaum, Uber Aromatische Tellurverbindungen (I. Mitteilung uber Organometallverbindungen), *Analen der Chemie,* Vol. 523, 1936, pp. 211–221, cited above, describes the preparation of bis(4-acetamidophenyl)ditelluride. Other para amido substituted aromatic ditellurides can be prepared by analogous procedures.

The ortho amido substituted aromatic ditellurides are novel compounds. Preparation of these compounds can be achieved in one approach by reducing an N-protonated or quaternized oxatellurazinium salt with hypophosphorous acid in an aqueous solution. If desired to enhance solubility, auxiliary organic solvents can be present. The organic auxiliary solvents can be chosen from a wide range of relatively unreactive organic solvents. For example, acetonitrile, dimethylsulfoxide, dimethylformamide, dichloromethane, methanol, ethanol, or isopropyl alcohol, can be employed as an auxiliary solvent. The R in formula (III) above is supplied by the protonating hydrogen atom or quaternizing group of the oxatellurazinium salt while R' in formula (III) is supplied by the 6-position hydrogen or substituent of the oxatellurazinium ring.

Another approach to preparing the ortho amido substituted aromatic ditellurides of this invention is to ring open an aromatic tellurazolium salt by placing it in an aqueous solution, preferably a basic aqueous solution, such as a dilute alkali hydroxide solution. Oxidation by ambient air completes formation of the ortho amido substituted aromatic ditelluride. Again R in formula (III) corresponds to the ring nitrogen protonating hydrogen atom or quaternizing substituent.

To prepare an amido substituted aromatic tellurochalcogenide in which only a single tellurium atom is present, such as a compound satisfying formula (I) wherein Ch is sulfur or selenium, an ortho amido substituted aromatic ditelluride is reacted with bromide or chloride, which can be supplied from an aqueous salt solution. This cleaves the amido substituted aromatic ditelluride into two aromatic tellurochloride or bromide molecules, which can be further reacted by procedures generally known for preparing aromatic dichalcogenides to produce the desired amido substituted tellurochalcogenide. For example, the aromatic tellurochloride or bromide can be reacted in water with an anionic aromatic sulfide or selenide, such as an alkali benzene or naphthalene thiolate or selenolate, in the presence of a strong reducing agent, such as sodium borohydride, to produce an amido substituted aromatic tellurosulfide or telluroselenide satisfying formula (I).

EXAMPLES

The following examples further illustrate the invention. The prefix E is employed to identify example compounds while the prefix C is employed to identify control compounds.

Example 1

The superior fog inhibiting activity of the ortho amido substituted aromatic ditelluride E 1 over its selenium and sulfur analogs is shown in Table I. These compounds were evaluated in a polydisperse sulfur plus gold sensitized silver bromoiodide emulsion. The compounds were added at the levels indicated and coated on cellulose acetate support to achieve a silver coverage of 4.89 g/m$^2$ and a gelatin coverage of 11.09 g/m$^2$. Samples of the coatings were exposed to a tungsten light source in an Eastman 1B Sensitometer through a wedge spectrograph. The coatings were developed for five minutes in a hydroquinone-Elon ®(p-aminophenol hemisulfate) developer, fixed, washed and dried. Samples of each of the coatings were incubated for two weeks at 49° C. under 50 percent relative humidity before being exposed and processed as described above. A characteristic (density vs log exposure) curve was plotted for each coating. The sensitivity and fog data was determined from these curves. The results are recorded in Table I.

The data in Table I demonstrate superior fog inhibiting activity of the amido substituted aromatic ditelluride over the corresponding diselenide (which in turn was superior to the corresponding aromatic disulfide). The behavior of the ditelluride was not an extrapolation of any trend from the disulfide to the diselenide. The amido substituted aromatic ditelluride caused sensitivity (speed) loss in fresh coatings which was much more significant than for the corresponding diselenide or disulfide. On incubation however, the sensitivity improved. Clearly the reverse was observed for the corresponding diselenide and disulfide. The ideal level of the amido substituted aromatic ditelluride was the lowest level, which was the opposite of the level needed for the corresponding diselenide.

TABLE 1

Comparisons of Bis[2-(N—methylacetamido)-phenyl] Ditelluride, Diselenide and Disulfide

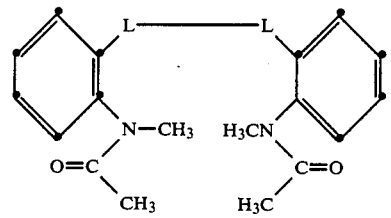

E-1 L = Te
C-2 L = Se
C-3 L = S

| Compound | Level mmole/ mole Ag | Fresh Relative Sensitivity | Fog | Incubation Relative Sensitivity | Fog |
| --- | --- | --- | --- | --- | --- |
| Control | — | 100 | 0.10 | 59 | 0.49 |
| E-1 | 0.05 | 74 | 0.06 | 107 | 0.08 |
|  | 0.10 | 60 | 0.08 | 69 | 0.06 |
|  | 0.30 | 19.5 | 0.05 | 21.5 | 0.05 |
| C-2 | 0.05 | 89 | 0.07 | 62 | 0.27 |
|  | 0.10 | 82 | 0.08 | 78 | 0.18 |
|  | 0.30 | 80 | 0.07 | 82 | 0.07 |
| C-3 | 0.05 | 102 | 0.08 | 36 | 0.45 |
|  | 0.10 | 95 | 0.09 | 41 | 0.47 |
|  | 0.30 | 97 | 0.08 | 54 | 0.42 |

Example 2

Other amido substituted aromatic ditellurides as well as another amido substituted aromatic diselenide and amido substituted aromatic disulfide are compared as fog inhibiting agents in the same manner as in Example 1. Their activity is recorded in Table II. It is apparent that the amido substituted aromatic ditellurides produce superior fog and speed/fog relationships even at concentrations approximately an order of magnitude lower than those of the amido substituted aromatic diselenide and amido substituted aromatic disulfide.

TABLE II

Comparisons of Amido Substituted Aromatic Ditelluride, Diselenide, and Disulfide

| Structure | Compound | Level mmoles/mole Ag | Fresh Relative Sensitivity | Fog | Incubation Relative Sensitivity | Fog |
| --- | --- | --- | --- | --- | --- | --- |
| Control | — | — | 100 | 0.08 | 80 | 0.80 |
| 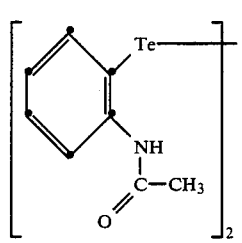 | E-4 | 0.05 | 100 | 0.07 | 121 | 0.23 |
|  |  | 0.15 | 83 | 0.06 | 58 | 0.18 |

TABLE II-continued
Comparisons of Amido Substituted Aromatic
Ditelluride, Diselenide, and Disulfide

| Structure | Compound | Level mmoles/mole Ag | Fresh Relative Sensitivity | Fog | Incubation Relative Sensitivity | Fog |
|---|---|---|---|---|---|---|
| 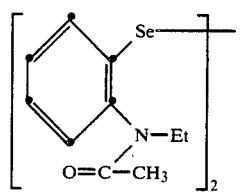 | C-5 | 0.15<br>1.50 | 74<br>45 | 0.29<br>0.32 | 118<br>71 | 0.35<br>0.32 |
| 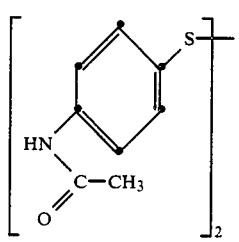 | C-6 | 0.15<br>1.50 | 69<br>39 | 0.06<br>0.05 | 126<br>87 | 0.32<br>0.21 |

Examples 3 through 6

The procedure of Example 1 was repeated, but with lower concentration levels of the amido aromatic ditelluride present in the emulsion layers. Their activity is recorded in Table III. It is apparent that the amido substituted aromatic ditellurides result in lower fog levels while producing superior speed/fog relationships than are realized in their absence.

solved in one liter of water at 40° to 45° C. To the clear solution hypophosphorous acid (50% in water)(20 ml) was added with vigorous stirring at room temperature. Stirring was continued for 2 hours and 30 minutes at room temperature. The product was isolated by filtration, washed with water and air dried on a suction filter. The yield was 18.8 g (85% of theory).

Example 8

TABLE III
Fog and Relative Sensitivity Effects of
Amido Substituted Aromatic Ditellurides

| Structure | | Compound | Level mmoles/ mole Ag | Fresh Relative Sensitivity | Fog | Incubation Relative Sensitivity | Fog |
|---|---|---|---|---|---|---|---|
| Control | | — | — | 100 | 0.13 | 40 | 0.74 |
| 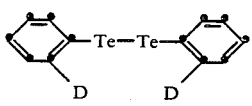 | D = —N(CH₃)—C(=O)—CH₃ | E-1 | .004<br>.02<br>.06<br>.10 | 95<br>94<br>85<br>85 | 0.12<br>0.11<br>0.09<br>0.08 | 45<br>63<br>95<br>82 | 0.72<br>0.49<br>0.17<br>0.09 |
| 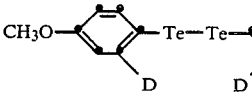 | D = —N(H)—C(=O)—CH₃ | E-7 | .004<br>.02<br>.06<br>.10 | 100<br>95<br>82<br>87 | 0.12<br>0.12<br>0.11<br>0.10 | 54<br>68<br>76<br>65 | 0.65<br>0.48<br>0.28<br>0.18 |
| 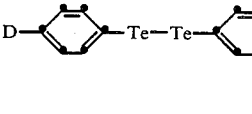 | D = —N(CH₃)—C(=O)—CH₃ | E-8 | .004<br>.02<br>.06<br>.10 | 100<br>91<br>50<br>35.5 | 0.12<br>0.11<br>0.09<br>0.08 | 63<br>76<br>76<br>58 | 0.63<br>0.43<br>0.21<br>0.13 |
| 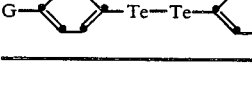 | D = —N(H)—C(=O)—OC₂H₅ | E-9 | .004<br>.02<br>.06<br>.10 | 94<br>57<br>23<br>14.5 | 0.11<br>0.08<br>0.07<br>0.06 | 71<br>71<br>13.4<br>24.5 | 0.56<br>0.23<br>0.11<br>0.09 |

Example 7

Bis(2-acetamido-4-methoxyphenyl)ditelluride $C_{18}H_{20}N_2O_4Te_2$
mw = 583.56
1,1,1-Trichloro-6-methoxy-3-methyl-2,1,4-benzoxatellurazinium, inner salt (30 g, 0.075 mole) was dis- Bis[2-(N-methylacetamido)phenyl]ditelluride $C_{18}H_{20}N_2O_2Te_2$
mw = 551.56
1,1,1-Tribromo-3,4-dimethyl-2,1,4-benzoxatellurazinium, inner salt (0.50 g, 0.001 mole) was suspended in water (20 ml). Hypophosphorous acid (2 ml) was added. Dichloromethane (20 ml) was added, and the mixture, contained in an aluminum foil wrapped flask, was stirred vigorously for about 2 hours. The dichloromethane containing the product was separated. The solvent was removed under reduced pressure, and the oily organge to brown residue was taken up in a minimum amount of a hot isopropanol-water mixture. The product crystallized on cooling and was isolated by filtration. The melting point of the product was 139° to 141° C.

APPENDIX

N-Protonated and quaternized aromatic tellurazolium salts and their preparations are taught by Gunther et al U.S. Ser. No. 660,155, filed Oct. 12, 1984, titled PHOTOGRAPHICALLY USEFUL CHALCOGENAZOLES, CHALCOGENAZOLINES, AND CHALCOGENAZOLINIUM AND CHALCOGENAZOLIUM SALTS, commonly assigned. One disclosed preparation process synthesizes N-protonated aromatic oxatellurazinium salts to be employed as intermediates.

Quaternized oxatellurazinium salts and their preparations are taught by Pryzklek et al U.S. Ser. No. 719,841, filed Apr. 4, 1985 concurrently herewith and commonly assigned, titled QUATERNIZED TELLURIUM SALT FOG INHIBITING AGENTS FOR SILVER HALIDE PHOTOGRAPHY. Przyklek-Elling et al employs quaternized aromatic tellurazolium salts as starting materials for the preparation of quaternized aromatic oxatellurazinium salts. The process of Przyklek-Elling et al has equal applicability to the preparation of N-protonated aromatic oxatellurazium salts.

This appendix sets forth procedures for preparing the N-protonated or quaternized aromatic oxatellurazinium salts as well as the N-protonated or quaternized aromatic tellurazolium salts employed as starting materials for preparing the ortho amido substituted aromatic tellurochalcogenides of this invention.

Useful starting materials for the practice of this invention can be represented by aromatic tellurazolium salts satisfying formulae (IV) and (V)

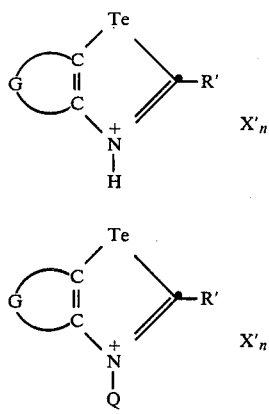

and aromatic oxatellurazinium salts satisfying formulae (VI) and (VII)

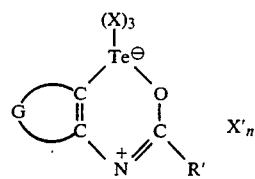

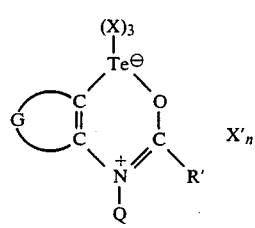

wherein
G corresponds to Ar or Ar';
R' is as previously defined;
Q is a quaternizing substituent;
X represents chloride or bromide as initially prepared, but which can be extended to halogen or pseudohalogen by subsequent substitution;
X' represents a charge balancing counter ion; and
n represents the integer 0 or 1.

An aromatic oxatellurazinium salt of formula (VI) or (VII) can be prepared by reacting a corresponding aromatic tellurazolium salt of formula (IV) or (V) with chlorine and bromine in the presence of oxygen. The reaction can be conveniently performed by dissolving the aromatic tellurazolium salt of formula (IV) or (V) in solution. Solvents can be chosen from among water and organic solvents, such as any of those previously described. Elemental bromine or chlorine can be dissolved in the aqueous solution containing the aromatic tellurazolium salt. For example, liquid bromine can be added directly to the aqueous solution. Chlorine can be dissolved in the aqueous solution by bubbling chlorine gas. Alternatively, elemental bromine or chlorine can be generated in the aqueous solution by adding bromine or chlorine releasing compounds and a strong nonoxidizing acid, such as hydrochloric acid, hydrobromic acid, sulfuric acid, fluoroboric acid, a sulfonic acid, or phosphoric acid. For example, elemental bromine can be readily released into the aqueous solution by introducing an alkali bromate, N-bromosuccinamide, or alkali hydrobromite. Elemental chlorine can be conveniently released by introducing an alkali hypochlorite. The ring oxygen atom can be supplied by the spontaneous interaction of ambient air.

Generally the reaction of the aromatic tellurazolium salt and the elemental bromine or chlorine present in the aqueous solution occurs spontaneously at room temperature. In most instances the reaction appears to occur substantially instantaneously.

Although the compound of formula (VI) or (VII) as initially prepared restricts the choice of X to chloride or bromide, if desired, the chloride or bromide in the formula (V) compound can be displaced by iodide or a pseudohalogen by treatment with an iodide or pseudohalogen salt. The term "pseudohalogen" is employed to designate any one of the recognized class of substituents known to approximate the substituent properties of halogen, such as a cyano, thiocyanate, or hydroxy substituent. Thus, X is formulae (VI) and (VII)

can be halogen (employed here and elsewhere to designate generically chloride, bromide, or iodide) or pseudohalogen. In a specifically preferred form X is chloride or bromide.

The quaternizing substituent Q in formulae (VII) in general corresponds to the quaternizing substituent present in the quaternized aromatic tellurazolium salt of of formula (V). However, since preparation of the quaternized oxatellurazinium salt requires bromine or chlorine treatment, it is apparent that any quaternizing substituent of the aromatic tellurazolium salt that is susceptible to bromine or chlorine addition will be modified. For example, quaternizing groups containing vinyl or acetylenic unsaturation will be bromine or chlorine substituted if present in the quaternized aromatic tellurazolium salt.

The choice of quaternizing substituents Q can be better appreciated by noting that the quaternized aromatic tellurazolium salt of formula (V) can be prepared by reacting a tellurazole satisfying formula (VIII)

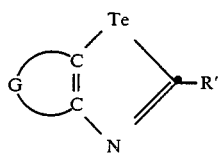

(VIII)

with a quaternizing agent. In one preferred form the quaternizing agent is a sulfonic acid ester containing the quaternizing radical Q as the base derived moiety of the ester. Specifically preferred quaternizing agents are strong quaternizing agents, such as poly(fluoro)alkylsulfonic acid esters, such as alkyl, aryl, alkenyl, alkynyl, aralkyl, or alkaryl esters of poly(fluoro)alkylsulfonic acid. Perfluorinated alkylsulfonic acid esters are particularly preferred quaternizing agents (e.g., trifluoromethylsulfonic acid esters). Arylsulfonic acid esters, such as para-toluenesulfonic acid esters, are also strong quaternizing agents. 1,3,2-Dioxathiane-2,2-dioxide and 1,3,2-di-oxathiolane-2,2-dioxide have also been demonstrated to be useful quaternizing agents. Including electron donating ring substituents in the aromatic nuclei forming G facilitates quaternization while strongly electron withdrawing substituents require strong quaternizing agents to be employed when quaternization occurs after tellurazole ring formation.

The aromatic tellurazole of formula (VIII) can be conveniently prepared by treating the N-protonated aromatic tellurazolium salt of formula (IV) with a base. The protonated tellurazolium salt can be prepared in turn by one of the following alternative processes.

A first process for preparing a protonated tellurazolium salt satisfying the general formula (IV) comprises reacting a starting material of the formula

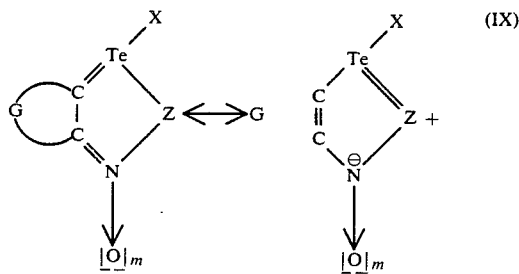

with a strong alkaline reducing agent,
acylating with a compound of the formula

(X)

and
treating with a strong nonoxidizing acid,
wherein
G represents the atoms completing a fused aromatic nucleus,
R' is an optionally substituted hydrocarbon moiety,
m is zero or 1,
X is halogen or pseudohalogen,
Y is halogen or R'—C(O)—O—,
Z is —O— or —N(R")—, and
R" is an aromatic nucleus.

A second process for preparing a protonated tellurazolium salt satisfying general formula (IV) comprises reacting a starting material of the formula

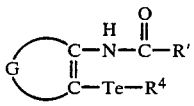

(XI)

with phosphoryl chloride or bromide wherein:
G represents the atoms completing an aromatic nucleus,
R' represents hydrogen, an optionally substituted hydrocarbon moiety, or a —C(O)M group, wherein M is chosen to complete an aldehyde, acid, ester, thioester, or salt, and
R⁴ represents a leaving group.

A third process for preparing a protonated tellurazolium salt satisfying general formula (IV) comprises
reacting a starting material of formula (VI) with a strong alkaline reducing agent and
treating with a strong nonoxidizing acid.
The starting material according to formula (VI) is prepared by reacting a compound according to formula (XII)

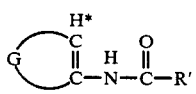

(XII)

with tellurium tetrachloride or tellurium tetrabromide at an elevated temperature,
wherein:
H* is an activated hydrogen atom, G represents the atoms completing an aromatic nucleus, R' represents an aliphatic or aromatic group comprised of a hydrocarbon moiety optionally linked through a divalent oxy, thio, or carbonyl linkage, an amino group, an amido group, a formamidine disulfide group, or a —C(O)M group, wherein M is chosen to complete an acid, ester, thioester, or salt, and X represents chloride or bromide or a halogen or pseudohalogen substituted therefor after preparation.

The first process for preparing a protonated tellurazolium salt satisfying formula (IV) described above employs a starting material satisfying formula (IX). When m is zero and Z is —N(R")—, the starting material can be (2-phenylazophenyl-C,N')tellurium(II) chloride, the preparation of which is described by Cobbledick et al, cited above. Although Cobbledick et al employed chloride as the halogen corresponding to X in formula (IX), it is apparent from the reported synthesis that X can be a halogen or pseudohalogen substituent. Similarly, G and R" can be varied merely by substituting for one or both of the phenyl groups employed in the phenylazophenyl employed by Cobbledick et al an alternative aromatic nucleus.

In an alternative form the first process can employ a starting material according to formula (IX) in which m is zero and Z is oxygen. This compound can be formed by placing in solution an optionally substituted α-tetralone, hydrochloric or hydrobromic acid, tellurium dioxide, and hydroxylamine. This reaction has the advantage that all of the required materials are readily available at relatively low cost. Alcohols are convenient solvents for the reaction, although other nonreactive organic solvents can be employed. Heating is not required, but can accelerate the reaction. The material of formula (IX) forms a solid phase which can be separated by routine filtering and washing steps. Both unsubstituted α-tetralone and various substituted derivatives are useful. Preferred α-tetralones can be represented by the formula (XIII):

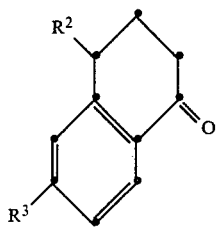

(XIII)

wherein $R^2$ and $R^3$ are independently selected from among hydrogen, halogen, alkyl, and alkoxy. Since $R^2$ and $R^3$ are naphtho ring substituents in the tellurazolium salt ultimately produced, it is apparent that the number of carbon atoms in the alkyl and alkoxy substituents can be widely varied. Instead of employing an α-tetralone, as described above, it is possible to employ a substituted or unsubstituted acenaphthen-1-one.

In general alkyl substituents and moieties of the tellurazolium salts and their derivatives are limited only by physical considerations, such as solubility, mobility, and molecular bulk. Generally alkyl and other aliphatic moieties of the tellurazolium salts and their derivatives of this invention are contemplated to contain up to 18 or more carbon atoms. Since increasing molecular bulk, except as sometimes required to reduce mobility, is seldom desirable in photographic applications, the preferred aliphatic hydrocarbon moieties contain up to 6 carbon atoms, with the lower alkyls (i.e., methyl, ethyl, propyl, and butyl) being preferred. In general, references to cycloalkyl indicate groups having 4 to 10 carbon atoms in a ring, with 5 or 6 ring carbon atoms being preferred.

Instead of preparing the starting material of formula (IX) wherein m is zero and Z is oxygen in the manner described above, an oxime of an α-tetralone or acenaphthen-1-one described above can be reacted with tellurium tetrahalide, preferably tellurium tetrachloride or tellurium tetrabromide. In this and subsequent descriptions of employing tellurium tetrahalides as reactants it should be borne in mind that similar results can usually be obtained by reacting, before or during the α-tetralone or acenaphthen-1-one or reaction, a soluble halide salt, such as an alkali or alkaline earth halide, with tellurium dioxide. This is believed to generate a tellurium tetrahalide. A carboxylic acid can be employed as a solvent for the reaction, and the reaction can be accelerated by heating. The starting material of formula (IX) forms a solid phase which can be separated by routine filtering and washing procedures. The preferred α-tetralone oximes correspond to the preferred α-tetralones and can be represented by formula (XIV):

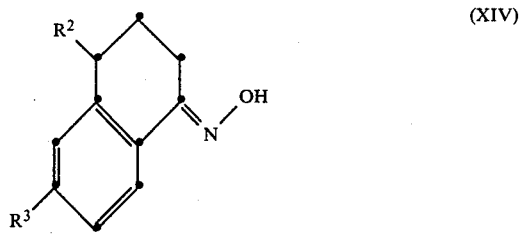

(XIV)

wherein $R^2$ and $R^3$ are chosen as described above.

In a third general form of the starting material of formula (IX) m can be 1 and Z oxygen. This form of the starting material of formula (IX) can be prepared by reacting with tellurium tetrahalide a carbocyclic aromatic compound activated for electrophilic substitution. Although naphthalene is illustrative of a fused ring carbocyclic aromatic compound that has been activated for electrophilic substitution, it is generally easiest to activate benzene. Activation can be achieved by employing electron donating substituents, such as hydroxy, hydroxyalkyl, alkyl, alkoxy, aryloxy, hydroxyaryl, amino, and groups of similar negative Hammett sigma values, singly or in combination. The reaction can be carried out in an organic solvent such as a liquid hydrocarbon (e.g., benzene or cyclohexane), a halohydrocarbon (e.g., chlorobenzene or chloroform), a nitrohydrocarbon (e.g., nitromethane), or acetonitrile while heating to reflux. Formation of the starting material of formula (IX) can be completed by nitrating and then treating with a reducing agent. Strong reducing agents can be employed in precisely stoichiometric concentrations or less. It is generally preferred to employ a mild or dilute reducing agent. Nitric acid in a suitable diluent, such as water or carboxylic acid, can be used for nitrating while hypophosphorous acid can be employed as the mild reducing agent. The synthetic route described above can be modified by a preliminary treatment with the mild reducing agent before nitrating and employing a strong nonoxidizing acid after nitrating and before employing the mild reducing agent a second time. In general the strong nonoxidizing acids contemplated for use in this and other steps of the preparation procedures herein described include acids such as hydrochloric acid, hydrobromic acid, sulfuric acid, fluoroboric acid, a sulfonic acid, and phosphoric acid.

A particularly preferred starting material prepared by the process described in the preceding paragraph can be represented by formula (XV):

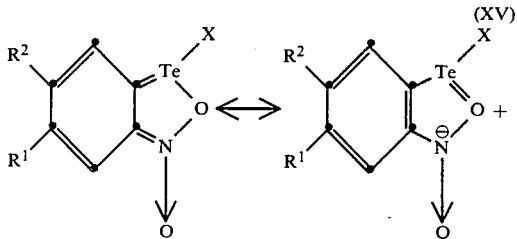

wherein at least one of $R^1$ and $R^2$ and preferably both are chosen from among hydroxy, hydroxyalkyl, alkyl, alkoxy, aryloxy, hydroxyaryl, and amino groups. Alternately $R^1$ and $R^2$ together can form an alkanediyldioxy linkage—e.g., a —O—$(CH_2)_n$—O— linkage, where n is preferably from 1 to 3. X is halogen or pseudohalogen, as previously described.

Once the starting material of formula (IX) has been prepared, regardless of the choice of alternative preparation routes described above, it is treated with a strong alkaline reducing agent, such as an alkali borohydride (e.g., lithium, sodium, or potassium borohydride). The reaction product is then acylated with a compound according to formula (X). From the values of Y identified above, it is apparent that the acylating agent can be either acyl halide, such as acetyl chloride or acetyl bromide, or an acid anhydride, such as acetic anhydride. It is also apparent that the acyl halide or acid anhydride also provides the 2-position substituent in the protonated tellurazolium salt satisfying formula (IV). Generally R' is a methyl group, but a wide variety of alternatives can be generated readily, if desired. When the acylating agent is acetyl halide or acetic anhydride, the 2-position substituent is methyl. By varying the acyl halide or acid anhydride employed, the 2-position substituent of the tellurazolium salt can take the form of various hydrocarbon moieties, such as alkyl, cycloalkyl, alkaryl, aryl, aralkyl, and various substituted derivatives, such as those containing alkoxy, alkylthio, halo, amino, amido, and similar substituents.

Though not isolated, it is believed that acylation produces tellurazolines. To avoid opening of the tellurium containing ring, the additional step of producing the stable corresponding protonated tellurazolium salt is undertaken by treatment with a strong nonoxidizing acid, such as any of those mentioned above.

The second process for preparing protonated tellurazolium salts according to formula (IV) allows a somewhat more general selection of R' or 2-position ring substituents as compared to the first process. The starting material employed for this process is represented by formula (XI). When the second process is employed, R' in the starting material of formula (XI) and the protonated tellurazolium salt prepared satisfying formula (IV) can include in addition to any of the optionally substituted hydrocarbon moieties discussed above in connection with the first process hydrogen or a —C(O)M group, wherein M is chosen to complete an aldehyde, acid, ester, thioester, or salt (e.g., —C(O)H, —C(O)OH, —C(O)OCH$_3$, —C(O)SCH$_3$, or —C(O)ONa). When M completes an ester or thioester, the esterifying moiety can take any of the hydrocarbon or substituted hydrocarbon form(s) previously described by reference to R'.

$R^4$ in formula (XI) forms no part of the protonated tellurazolium salt ultimately produced. Thus, $R^4$ can take the form of any convenient group that can be displaced under treatment with phosphoryl chloride to permit ring closure. Treatment with phosphoryl chloride eliminates Cl—$R^4$. Thus, any group that can be eliminated as the chloride can be chosen as the leaving group. For example, $R^4$ can be chosen from among the same hydrocarbon moieties described above in connection with R'. Since R' forms no part of the protonated tellurazolium salt ultimately produced, it is generally most convenient to select $R^4$ from among lower alkyl substituents.

The starting material of formula (XI) can be prepared from known tellurium compounds by several alternative procedures. One preferred approach is to start with a compound according to formula (IX) in which m is zero and Z is —N(R'')—, as previously described. This compound is treated with a strong alkaline reducing agent, such as previously described. Thereafter, acylation is performed using an acylating agent according to formula (X), as previously described. This produces the material of formula (XI). To produce the starting material of formula (XI) by another procedure, after treating the above compound of formula (IX) with a strong alkaline reducing agent, the reaction product is reacted with X—$R^4$, where X is halide, and then acylated with formic acid. In this instance R' in formula (XI) is hydrogen. By employing other acylating agents R' can take any one of the other forms of formula (XI).

A third process for preparing a protonated tellurazolium salt according to formula (IV) comprises employing a starting material according to formula (VI). X in formula (VI) can be halogen or pseudohalogen, as previously described. R' in the starting material of formula (VI) can take an even greater variety of forms than described above in connection with formula (XI). R' in the starting material of formula (VI) and the protonated tellurazolium salt prepared satisfying formula (IV) can include an aliphatic or aromatic group comprised of a hydrocarbon moiety (e.g., alkyl, aryl, alkaryl, or aralkyl moiety) optionally linked through a divalent oxy, thio, or carbonyl linkage (e.g., an alkoxy, aryloxy, alkaryloxy, aralkyloxy, alkylthio, arylthio, alkarylthio, aralkylthio, or acyl moiety); an amino group, including primary, secondary and tertiary amines; an amido group (e.g., acetamido, butryamido, 1-ureido, 3-phenyl-1-ureido, and 3-methyl-1-ureido); a formamidine disulfide group (e.g., formamidine disulfide and N'-ethyl-N'-methyl-α, α'-dithiobisformamidine groups); or a —C(O)M group, wherein M is chosen to complete an aldehyde, acid, ester, thioester, or salt (e.g., —C(O)H, —C(O)OH, —C(O)OCH$_3$, —C(O)SCH$_3$, or —C(O)ONa). The starting material is reacted with a strong alkaline reducing agent, such as described above, and the resulting product is reacted with a strong nonoxidizing acid, such as also described above, to produce the desired protonated tellurazolium salt. By suitable treatment, (e.g., reduction or hydrolysis), the formamidine disulfide can, if desired, be converted to a thioureido group once the protonated tellurazolium salt has been formed. (The structure of formamidine disulfide is described in *International Union of Pure and Applied Chemistry, Nomenclature of Organic Chemistry*, Butterworths, London, 1965, Section 951.5.) When R' is a primary amino group, it is in fact in one tautomeric form an imino group, which provides a highly convenient starting material for the synthesis of azacyanine dyes.

When any commonly available compound of formula (XII) is melted or heated in a suitable solvent (e.g., acetonitrile, butyronitrile, or chloroform) with tellurium tetrachloride or tellurium tetrabromide, the material of formula (VI) is produced. Heating to a temperature of at least 60° C. up to about 140° C. is contemplated, with temperatures of from about 110° to 120° C. being preferred. As noted above, G in formula (XII) is chosen so that the aromatic nucleus which it completes is activated in the position ortho to the amido substituent. The aromatic nucleus completed by G as well as R' can progress unaltered from the compound of formula (XII) to the protonated tellurazolium salt of formula (IV).

To obtain the tellurazole of formula (VIII) corresponding to the protonated tellurazolium salt prepared as described above treatment with a base, such as ammonium hydroxide, an alkali hydroxide, or an alkali carbonate or bicarbonate, can be undertaken. Procedures for performing the same operation on known chalcogenazolium salts are directly applicable.

Instead of forming a quaternized aromatic tellurazolium salt by first preparing a protonated aromatic tellurazolium salt, converting it to the corresponding tellurazole, and then quaternizing, an alternative approach for preparing quaternized tellurazolium salts according to formula (V) is to employ a starting material according to formula (IX) wherein m is zero, indicated specifically by formula (XVI):

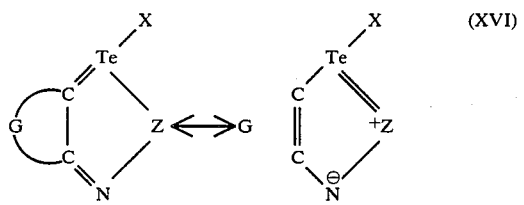
(XVI)

wherein G, X, and Z are as indicated in formula (IX). The starting material is first treated with a strong alkaline reducing agent, which can be selected from among those described above. The reaction product is then treated with an oxidizing agent, such as oxygen, a peroxide, a disulfide, or a sulfoxide, to produce the compound of formula (XVII)

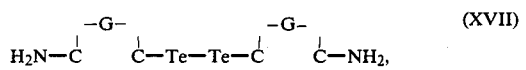
(XVII)

which is treated with an aldehyde, treated with a strong alkaline reducing agent, such as described above, and then treated with an acylating agent according to formula (X), as described above, and a strong nonoxidizing acid, also as described above. Although treatment with an oxidizing agent is preferred, no separate oxidizing step is required. Ambient air will spontaneously perform such oxidation, and treatment with the aldehyde is sufficient in an inert atmosphere. Employing this approach, a variety of quaternizing substituents can be introduced in the salt of formula (V) in addition to those provided by strong quaternizing agents, merely by appropriate selection of the aldehyde. Thus, Q in formula (V) can take the form of an optionally substituted hydrocarbon residue of an aldehyde quaternizing substituent, such as alkyl, alkenyl, alkynyl, or aralkyl moieties as well as substituted derivatives, such as oxy, thio, sulfo, sulfonyl, sulfato, halo, or carboxy substituted derivatives, often incorporated to modify solubility or other physical properties. Sulfoalkyl and sulfatoalkyl quaternizing substituents having from 1 to 6 carbon atoms are specifically preferred.

PREPARATIONS

The following illustrate preparations of starting materials useful in the practice of this invention. Preparations of compounds of types that have been previously published are labeled by letters (e.g., A, B, C, etc.). Preparations of starting materials not previously published are designated by appendix example (appexample) numbers (e.g., Appexample 1, Appexample 2, etc.).

A. Preparation of 2-Phenylazophenyltellurium Trichloride

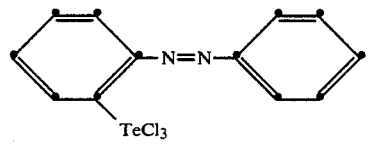

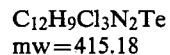

$C_{12}H_9Cl_3N_2Te$
mw=415.18

A two liter, 3-necked flask was fitted with mechanical stirrer (Teflon ® blade), reflux condenser and nitrogen inlet. A gas outlet from the top of the condenser was connected to a gas bubbler dipping into a magnetically stirred 1000 ml beaker containing 200 ml distilled water and a little phenolphthalein indicator. The system was sufficiently gas tight so that a very gentle stream of nitrogen produced consistent bubbles in the indicator solution.

Into the flask were placed 100 g (0.55 mole) azobenzene, 134 g (0.5 mole) tellurium tetrachloride, and 66 g (0.5 mole) anhydrous aluminum chloride. 1,2-Dichlorobenzene (500 ml) was added, the apparatus closed, the nitrogen flow started, and the mixture stirred until an orange-brown solution was obtained. Five ml of 1N sodium hydroxide were then added to the indicator solution, and the flask contents were heated to reflux with brisk stirring. The start of the reaction was marked by loss of the indicator color. Measured volume increments of 1N sodium hydroxide were then added to the beaker each time the indicator color discharged. Incremental volume and elapsed time of addition are tabulated below:

| Time Minutes | Vol. in NaOH ml |
|---|---|
| 0 | 5 |
| 6.5 | 50 |
| 13.0 | 100 |
| 20.0 | 150 |
| 28.0 | 200 |
| 36.5 | 250 |
| 46.0 | 300 |

| Time Minutes | Vol. in NaOH ml |
|---|---|
| 54.0 | 350 |
| 70.0 | 400 |
| 85.0 | 450 |
| 94.0 | 475 |

Boiling under reflux was continued until 475 ml 1N sodium hydroxide had been consumed. The flask contents were then permitted to cool to about 80° C. Methyl alcohol was then added very slowly to the rapidly stirred solution until the initial vigorous reaction ceased. A total of 500 ml methanol was then added and the mixture cooled in ice for more than one hour. The heavy granular crystalline precipitate was collected by filtration and washed with methanol until the methanol filtrate was pale yellow.

The light brown glittering crystals were dried in vacuum. A yield of 130.3 g (63% of theory), m.p. 261°–263° C. was obtained. The product contained small amounts of oxides that were removed by recrystallization from 1,2-dichlorobenzene. Elemental analyses of the recrystallized product were in agreement with the structural formula.

B. Preparation of 3,4-Dimethoxyphenyltellurium Trichloride $C_8H_9Cl_3O_2Te$
mw = 371.13

1,2-Dimethoxybenzene (veratrole, 13.8 g = 0.1 mole) and tellurium tetrachloride (26.9 g = 0.1 mole) were heated in chloroform (120 ml) for 2 hours under reflux and with stirring. After 30 minutes yellow crystals started to precipitate. The product (25.2 g, 67.9% of theory) was collected by filtration and dried in a vacuum oven, m.p. 162°–163° C. (dec. with gas evolution). The mass spectra were in agreement with that of the structural formula.

C. Preparation of Bis(3,4-dimethoxyphenyl)ditelluride $C_{16}H_{18}O_4Te_2$
mw = 529.42

3,4-Dimethoxyphenyltellurium trichloride (37.2 g = 0.1 mole) was dissolved in absolute ethanol (500 ml), and the slightly turbid solution was filtered. To the rapidly stirred solution was added, at room temperature, 50% aqueous hypophosphorous acid (30 ml, ≃0.3 mole) as rapidly as possible. There was a brief appearance of a brown solution color, before the entire solution set to a mass of black fibrous crystals. The product was collected after 15 minutes by filtration using rubber dam to compact the highly solvated crystal mass. The product was washed with water and then air dried to yield 25.2 g, 95% of theory, black fibrous crystals, m.p. 134°–136° C. Recrystallization from isopropanol raised the m.p. to 136°–139° C. C, H and Te elemental analyses were in agreement with the structural formula.

λ-max = 305 nm.
ε-max = 1.006 × 10$^4$.

APPEXAMPLE 1

1-Chloro-5,6-dimethoxy-2,1,3-benzoxaztellurazole-N-oxide

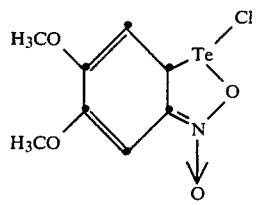

$C_8H_8ClNO_4Te$
mw = 345.21

A. By nitration of product of Preparation C

Bis(3,4-dimethoxyphenyl)ditelluride (10 g = 0.018 mole) was added in small portions to 70 mole percent nitric acid (15 ml) with stirring and chilling in ice. The material dissolved rapidly with emission of nitrous fumes. The mixture was then warmed at ≃40° C. for 30 minutes and subsequently stirred at room temperature for one hour. Emission of orange fumes was no longer observed. Water (150 ml) was then added to the orange solution resulting in a yellow precipitate, which (5 g) was mixed with ethanol (100 ml) and concentrated hydrochloric acid (20 ml), then diluted with water to 200 ml (just prior to occurrence of precipitation). Hypophosphorous acid (5 ml of 50 mole percent) was then added. During 15 minutes of stirring at room temperature, a deep red precipitate appeared which was collected by filtration. The product was recrystallized from absolute ethanol (450 ml) to give red prisms, (2.5 g), m.p. 197°–200° C. The yield by this procedure calculated to be ≃32%.

B. By nitration and reduction of product of Preparation B 3,4-Dimethoxyphenyltellurium trichloride (74 g = 0.2 mole) was suspended in glacial acetic acid (200 ml) in a 1500 ml Erlenmeyer flask. Nitric acid (18 g of 70% = 0.2 mole) was added gradually to the stirred mixture, which caused formation of a clear, red solution and a mildly exothermic reaction. Stirring was continued for one hour at room temperature, then ethanol (1000 ml) and hypophosphorous acid (24.0 g of 50 weight percent aqueous) were added in order. Over a period of 30 minutes there occurred crystallization of a red solid, which was collected by filtration to give 47.3 g, 68.8% of theory, m.p. 199°–200° C. The material was identical to product isolated by procedure A. Elemental analyses were in agreement with that calculated for the structural formula.

APPEXAMPLES 2–5

Appexamples 2 through 5 illustrate the preparation of compounds according to the following general formula

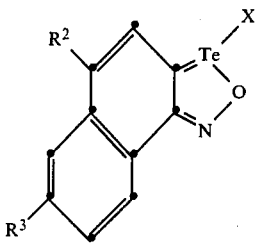

Appexample 2

3-Chloronaphth[2,1-c]-1,2,5-oxatellurazole,
$R^3=R^2=H$, $X=Cl$ $C_{10}H_6ClNOTe$
mw = 319.22

Tellurium dioxide (80 g, 0.5 mole) was dissolved in concentrated hydrochloric acid (200 ml, 2.0 moles) with stirring. When solution was complete, a suspension of hydroxylamine hydrochloride (69 g, 1.0 mole) in ethyl alcohol (300 ml) was added. When all solid was dissolved, α-tetralone (73 g, 0.5 mole) in ethyl alcohol (1200 ml) was added. The clear reaction mixture rapidly turned red and dark crystals began to form within an hour. After the reaction mixture had been kept five days at room temperature, the product was isolated by filtration and dried in a vacuum. Yield 123.2 g.

The product was separated from elemental tellurium by continuous extraction with dichloromethane in a Soxhlet extractor, using about 1300 ml of solvent. Chilling the extract yielded a first crop of 84.9 g. Diluting the filtrate with twice its volume of heptane yielded a second crop of 6.1 g. The combined yield of 91.0 g represented a 57% yield. mp. 182°–183° C. λ-max (in pyridine) was 503 nm. ε-max=0.82×10⁴. C, H, Cl, N, O and Te elemental analyses results and the mass spectra were in agreement with those expected for the structural formula.

Appexample 3

3-Bromonaphth[2,1-c]-1,2,5-oxatellurazole,
$R^3=R^2=H$, $X=Br$ $C_{10}H_6BrNOTe$
mw = 363.68

Alpha-tetralone oxime (24 g=0.05 mole), tellurium dioxide (35 g=0.22 mole), lithium bromide (60 g), and acetic acid (350 ml) were combined, and the mixture was heated to a gentle boil for 20 minutes. The precipitated solid was collected by filtering the reaction mixture hot and washing the product with water to give 38.9 g, 71% of theory, of a deep maroon solid. The product was recrystallized from carbon tetrachloride (m.p. 183°–185° C.). Elemental analyses and the mass spectra were in agreement with the those expected for structural formula.

Appexample 4

3-Chloro-5-methylnaphth[2,1-c]-1,2,5-oxatellurazole,
$R^3=H$, $R^2=CH_3$, $X=Cl$ $C_{11}H_8ClNOTe$
mw = 333.24

Tellurium dioxide (79.5 g=0.5 mole) was dissolved in concentrated hydrochloric acid (200 ml). Hydroxylamine hydrochloride (35 g=0.5 mole) was added and then ethanol to bring the total volume to 2000 ml. To the slightly turbid solution was added 4-methyl-α-tetralone (80 g=0.5 mole) and the stirred mixture heated briefly to boil. The clear deep red solution was then kept overnight at room temperature. The solid mass of crystalline product was collected, washed well with water and dried in a vacuum oven at 90° C. to give a first crop (111.1 g) of dark red needles. The filtrate was heated once again and kept at room temperature for 24 hours. A second crop of 14.3 g crude product was obtained. The well-dried products was placed into a Soxhlet thimble and extracted with methylene chloride. The majority of purified product crystallized from the solvent during the course of the extraction to give a yield of 97.0 g=58.3% of theory, m.p. 196°–198° C. Elemental analyses results were in agreement with the structural formula. The ultraviolet and visible spectra in dichloromethane showed three maxima.

λ-max 507 nm; ε-max=1.21×10⁴;
λ-max 300 nm; ε-max=1.06×10⁴;
λ-max 256 nm; ε-max=2.30×10⁴;

Appexample 5

3-Chloro-7-methoxynaphth[2,1-c]-1,2,5-oxatellurazole,
$R^3=OCH_3$, $R^2=H$, $X=Cl$ $C_{11}H_8ClNO_2Te$
mw = 349.24

This compound was prepared in the same general way as the corresponding compound of Appexample 4, except that 6-methoxy-α-tetralone (88.1 g=0.5 mole) was used as the starting ketone. The step of heating of the reaction mixture to boil and then keeping it at room temperature was repeated three times, giving a combined crude yield of 84.8 g. Recrystallization by Soxhlet extraction with dichloromethane gave 72.5 g, 41.5% yield, of small dark needles (m.p. 237°–239° C.). Elemental analyses results were in agreement with the structural formula. The ultraviolet and visible spectra in dichloromethane showed four maxima.

510 nm; ε-max=0.89×10⁴;
454 nm; ε-max=0.93×10⁴;
312 nm; ε-max=0.81×10⁴;
245 nm; ε-max=2.63×10⁴.

Appexample 6

1-Chloroacenaphtho[1,2-d]-2,1,5-oxatellurazole

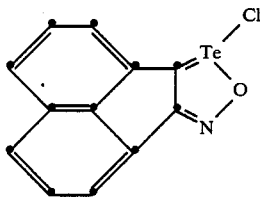

Acenaphthylen-1-one (83.5 g, 0.05 mole), hydroxylamine hydrochloride (35 g, 0.05 mole), and tellurium dioxide (80 g, 0.05 mole) were combined in ethanol (3 l). The mixture was heated to reflux and maintained at that temperature for an hour. It was then allowed to cool to room temperature and stirring at room temperature continued for 12 days. The solid was isolated by filtration, washed with ethanol, and air dried. Yield of brown powder was 106 g. This was extracted with toluene in a Soxlet extractor. The yield of product was 67.6 g, 46% of theory. The ultraviolet and visible spectra in dichloromethane solution showed four maxima, at 489.6, 429, 372, and 316 nanometers.

APPEXAMPLES 7-11

These examples refer to novel 1,1,1-trihalo(substituted) 2,1,4-benzotellurazinium, inner salts.

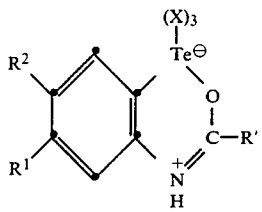

APPEXAMPLE 7

1,1,1-Trichloro-6-methoxy-3-methyl-2,1,4-benzoxatellurazinium, inner salt $R^1=OCH_3$, $R^2=H$, $R'=CH_3$, $X=Cl$ $C_9H_{10}Cl_3NO_2Te$
mw=398.05

3-Methoxyacetanilide, (34 g=0.2 mole) and tellurium tetrachloride (54 g=0.2 mole) were jointly stirred into chloroform (100 ml) in a 500 ml Erlenmeyer flask. After an initial solution had been formed, the mass set solid with a fine yellow precipitate. The mixture was immersed in an oil bath kept at 115° C. The mixture was manually stirred until all solids had redissolved or melted. After most of the chloroform had evaporated, there resulted a clear yellow melt that rapidly became opaque while gaseous HCl was being emitted. The temperature was raised to 120° C. and heating continued with occasional manual stirring until the entire mass had set to a brittle solid. The reaction was terminated after 2 hours. Ethanol was added to the still hot reaction mixture to disperse the product. Recrystallization from ethanol (1300 ml) yielded colorless needles (47.1 g, 59% of theory), m.p. 245°-246° C.

C, H, N and Te elemental analyses were in agreement with those calculated for the structural formula.

APPEXAMPLE 8

1,1,1-Trichloro-3,6-dimethyl-2,1,4-benzoxatellurazinium, inner salt $R'=R^1=CH_3$, $R^2=H$, $X=Cl$ $C_9H_{10}Cl_3NOTe$
mw=382.05

3-Methylacetanilide (m-acetotoluidide) (82 g=0.55 mole) and tellurium tetrachloride (148 g, 0.55 mole) were combined with chloroform (300 ml) and the mixture heated for 20 hours in an oil bath kept at 115° C. with continuous removal of HCl. The hot reaction product was dispersed in ethanol (200 ml) and the product collected by filtration to give a yield of 149 g, 71% of theory, colorless prisms, m.p. >300° C. For analyses the compound was recrystallized from boiling acetonitrile.

The elemental analyses were in agreement with those expected for the structural formula.

APPEXAMPLE 9

1,1,1-Trichloro-3,6,7-trimethyl-2,1,4-benzoxatellurazinium, inner salt $R'=R^1=R^2=CH_3$, $X=Cl$ $C_{10}H_{12}Cl_3NOTe$
mw=396.07

3,4-Dimethylacetanilide (56 g=0.37 mole) was combined with $TeCl_4$ (100 g, 0.37 mole) in acetonitrile (100 ml) and immersed in an oil bath, first for one hour at 120° C. and then for 3 more hours at 130° C. Additional acetonitrile was added, and the partial solution was chilled. The product was collected by filtration to give 74.7 g, 52% of theory, colorless crystals, m.p.>300° C. after darkening at >280° C. Recrystallization from acetonitrile required 400 ml solvent for 15 g of the substance. C, H, Cl, N and Te elemental analyses were in agreement with those expected for the structural formula.

Appexample 10

1,1,1-Trichloro-3-methyl-6-methylthio-2,1,4-benzoxatellurazinium, inner salt $R'=CH_3$, $R^1=SCH_3$, $R^2=H$, $X=Cl$ $C_9H_{10}Cl_3NOSTe$
mw=413.95

3-Methylthioactanilide (68 g=0.37 mole), prepared by acetylation of commercial 3-methylthioaniline, was combined with $TeCl_4$ (100 g=0.37 mole) in chloroform (100 ml). The mixture was heated for 3 hours in an oil bath kept at 130° C., then introduced hot into acetonitrile (300 ml), chilled, and filtered. A crystalline solid yielding 68 g, 49% of theory was obtained. For analysis the material was recrystallized from boiling acetonitrile (100 ml dissolves ≈4 g) with the aid of decolorizing charcoal and was recovered as lustrous, pale yellow prisms, m.p. 251°-253° C. The elemental analyses were in agreement with those expected for the structural formula.

APPEXAMPLE 11

1,1,1-Trichloro-6-hydroxy-3-methyl-2,1,4-benzoxatellurazinium, inner salt $R'=CH_3$, $R^1=OH$, $R^2=H$, $X=Cl$ $C_8H_8Cl_3NO_2Te$
mw=383.95

3-Hydroxyacetanilide (60 g=0.4 mole) and $TeCl_4$ (107.6 g=0.4 mole) were combined in acetonitrile (80 ml) and the mixture immersed for 2 hours in an oil bath maintained at 120° C. To the hot melt was then added enough acetonitrile to make a paste. The mixture chilled overnight and filtered with suction to give 86.5 g, 56% of theory, colorless crystalline solid. For analysis this was recrystallized from hot acetonitrile, where 25 g required 150 ml of solvent and gave a recovery of 10 g colorless needles, m.p. 247°-248° C. The elemental analyses were in agreement with that expected for the structural formula.

D. Preparation of Bis(2-acetamido-4-methoxyphenyl)ditelluride $C_{18}H_{20}N_2O_4Te_2$
mw=583.23

1,1,1-Trichloro-6-methoxy-3-methyl-2,1,4-benzoxatellurazinium, inner salt (Appexample 11) (5.0 g=0.0125 mole) was dissolved in 50% aqueous ethanol (200 ml). The solution heated to boil, and hydrazine (1 ml) was added with stirring. The deep orange solution was cooled slowly to room temperature to deposit fibrous needles which, upon filtration and drying, yielded a tan solid (3.25 g, 89% of theory), m.p. 181°-182° C.

APPEXAMPLES 12-17

Appexamples 12 through 17 illustrate the preparation of benzotellurazolium hydro salts.

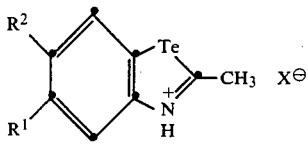

APPEXAMPLE 12

5,6-Dimethoxy-2-methylbenzo-3H-tellurazolium Chloride, $R^1=R^2=OCH_3$, $X=Cl$ $C_{10}H_{12}ClNO_2Te$ mw=341.26

1-Chloro-5,6-dimethoxy-2,1,3-benzoxatellurazole-N-oxide (Appexample 1) (103 g=0.3 mole) was suspended in a mixture of tetrahydrofuran (1000 ml) and methanol (150 ml) using a 3 liter, 3 necked flask fitted with a stirrer, a nitrogen inlet, a reflux condenser, and a powder addition funnel. Under nitrogen, sodium borohydride (61.5 g-1.6 mole) was added gradually to the stirred solution until the color was a pale cream. The amount of borohydride was determined empirically by the disappearance of the starting material red color. The reaction mixture was then chilled, and acetic anhydride was added until the color had turned a bright orange. This required 41.3 g=0.4 mole acetic anhydride. The reaction was permitted to proceed for 10 minutes, and then concentrated hydrochloric acid (300 ml) was added in one portion. The mixture turned black immediately, indicating that considerable quantities of tellurium had been generated.

The black mixture was stirred for another 30 minutes, then filtered to collect the precipitate. The solid was washed briefly with dichloromethane and air dried. The crude product was then added to 1200 ml boiling methanol containing a little hydrochloric acid and filtered hot with the aid of Celite ® diatomaceous earth. The filtrate was chilled overnight to give pale grey crystals (15.6 g). Two more crops of product were extracted from the black solid, giving a total yield of 21.34 g, 19.9% of theory. For further purification, the material was recrystallized from boiling water containing a little hydrochloric acid. The pale cream colored needles did not have a distinct melting point, but decomposed gradually >150° C.

APPEXAMPLE 13

5-Methoxy-2-methyl-3H-benzotellurazolium Chloride, $R^1=OCH_3$, $R^2=H$, $X=Cl$ $C_9H_{10}ClNOTe$ mw=311.24

1,1,1-Trichloro-6-methoxy-3-methyl-2,1,4-benzoxatellurazinium, inner salt (Appexample 7) (40 g=0.1 mole) was suspended in methanol (400 ml), and a solution of sodium hydroxide (8.0 g=0.2 mole) in water (75 ml) was added. This formed a clear solution which was placed into a vessel fitted with a stirrer, a nitrogen inlet, and a condenser. Under nitrogen, sodium borohydride (10.6 g, 0.28 mole) was added in small increments until the solution no longer turned red or orange with further additions, eventually turning colorless. Partway into the reduction, the mixture solidified, but liquified again as the reduction progressed. To the suspension, which had been cooled to ≃10° C., was then added concentrated hydrochloric acid (100 ml) in one portion. The precipitate was filtered after 15 minutes (yield 42 g dark solid), and the filtrate was chilled for a second crop of 12 g solids. The first crop was recrystallized from 700 ml of hot water containing a little hydrochloric acid. The recovery was 16.1 g of almost white needles. The second crop also contained sodium chloride. It was recrystallized from 125 ml methanol, also containing a little hydrochloric acid, to give 3.6 g product. The combined yield of 19.7 g represented 63% of theory. For analysis, the material was crystallized once more from acidic methanol, 105° C. (sinter), 130°-135° C. (turned black), no clear melt <270° C.

Appexample 14

2,5-Dimethyl-3H-benzotellurazolium Chloride, $R^1=CH_3$, $R^2=H$, $X=Cl$ $C_9H_{10}ClNTe$ mw=295.24

1,1,1-Trichloro-3,6-dimethyl-2,1,4-benzoxatellurazinium, inner salt (Appexample 8) (17.3 g=0.05 mole) was dissolved in a mixture of methanol (300 ml) and 1N sodium hydroxide (100 ml, 0.1 mole) in a vessel fitted with a nitrogen inlet, a condenser, and a magnetic stirrer. Through the condenser was added sodium borohydride until further addition no longer produced a transient orange color. This required about 3.0 g. The mixture was stirred for a few minutes under nitrogen, then concentrated hydrochloric acid (100 ml) was added in one portion. The mixture was clarified by filtration with Celite ®, then evaporated under reduced pressure to 200 ml, again filtered from inorganic salts and chilled overnight. Filtration yielded 9.15 g of colorless solid, which was rinsed with isopropanol and air dried. The material was not pure and contained inorganic salt contaminants.

Appexample 15

2,5,6-Trimethyl-3H-benzotellurazolium Chloride, $R^1=R^2=CH_3$, $X=Cl$ $C_{10}H_{12}ClNTe$ mw=309.25

1,1,1-Trichloro-3,6-7-trimethyl-2,1,4-benzoxatellurazinium, inner salt (Appexample 9) (39.6 g=0.1 mole) was placed into 400 ml of methanol in a 1000 ml, three necked flask fitted with a stirrer, a nitrogen inlet, a condenser, and a powder addition funnel. Sodium hydroxide (8.0 g=0.2 mole) in water (30 ml) was added, followed by sodium borohydride (8.56 g=0.225 mole) until the reduction mixture was a pale brown. This required heating to aid in dissolving the starting material and the initial reduction products. When the reduction was complete, the mixture was cooled to about 10° C., and concentrated hydrochloric acid (100 ml) was added in one portion. There was a granular black precipitate, which was removed by filtration. The filtrate was evaporated in vacuum to ≃250 ml, diluted with water to twice the volume, and stirred until crystallization was complete. A yield of 29.5 g, 94.8% of theory, was obtained. After two recrystallizations from methanol, the salt melted at 180°-184° C. (dec.).

Appexample 16

2-Methyl-5-methylthio-3H-benzotellurazolium Chloride, $R^1=SCH_3$, $R^2=H$, $X=Cl$

$C_9H_{10}ClNSTe$
mw=327.30

1,1,1-Trichloro-3-methyl-6-methylthio-2,1,4-benzotellurazinium, inner salt (Appexample 10) (20.7 g=0.05 mole) was placed in methanol (200 ml), and sodium hydroxide (4 g=0.1 mole) dissolved in water (10 ml) was added. The material did not completely dissolve. Sodium borohydride was added in portions with stirring under a nitrogen atmosphere. The starting material underwent vivid color changes to orange and then to blue with the addition of each portion of reducing agent. The mass became difficult to stir. Eventually, the reaction mixture became more liquid, though the orange color kept returning after each portion was added, as the rather insoluble starting material underwent the first reduction step. The reaction mixture was kept overnight under an atmosphere of nitrogen. The reduction was continued the next day by heating the mixture to near reflux temperature while sodium borohydride was being added. When the stage was reached where the reaction turned colorless after a portion was added and the orange color did not return upon further stirring (after the addition of 6.65 g=0.175 mole sodium borohydride), the mixture was cooled to ≃10° C. and concentrated hydrochloric acid (50 ml=0.5 mole) was added in one portion. The mixture turned orange, then yellow, and a copious beige precipitate formed. This was stirred for 45 minutes and then collected by filtration to yield 27.5 g solids. On recrystallization from methanol (300 ml), using Celite ® to clarify the solution, there were obtained 13.5 g, 81.9% of theory, cream colored needles, m.p. 130°–145° C. (dec.).

Appexample 17

5-Hydroxy-2-methyl-3H-benzotellurazolium Chloride, $R^1=OH$, $R^2=H$, $X=Cl$

$C_8H_8ClNOTe$
mw=297.23

1,1,1-Trichloro-6-hydroxy-3-methyl-2,1,4-benzoxatellurazinium, inner salt (Appexample 11) (19.2 g=0.05 mole) was dissolved in methanol (200 ml) with addition of sodium hydroxide (4 g) in water (20 ml). The reduction was carried out under a nitrogen atmosphere, using sodium borohydride (4.3 g=0.11 mole), after the addition of which the solution became clear. The reaction mixture was cooled to ≃10° C., and concentrated hydrochloric acid (65 ml) was added in one portion. Considerable black precipitate (11.7 g) formed, which was collected by filtration. The filtrate was evaporated to 50 ml and chilled to give a second crop (12.3 g). The products were recrystallized from isopropanol to give a combined yield of 9.45 g, 63.9% of theory, cream colored powder, m.p. 125°–132° C. (dec.).

APPEXAMPLES 18–25

Appexamples 18 through 25 illustrate the preparation of benzotellurazoles.

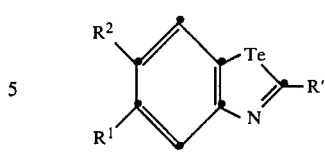

Appexample 18

2-Methylbenzotellurazole, $R'=CH_3$, $R^1=R^2=H$

$C_8H_7NTe$
mw=244.74

A mixture of 2-phenylazophenyltellurium trichloride (Preparation A) (20.7 g, 0.05 mole) and ethanol (200 ml) was placed in a 1 liter, 3 necked flask fitted with a nitrogen inlet, a powder addition funnel, and a reflux condenser. To the magnetically stirred mixture was added, under nitrogen, sodium borohydride (7.5 g, 0.2 mole) in increments at a rate sufficient to generate an elevated temperature. When the reaction mixture was nearly colorless the powder funnel was replaced by a stopper, taking care not to interrupt the flow of nitrogen. The flask was then chilled in an ice bath to 5° C. Acetic anhydride (5.5 g, 0.054 mole) was then added, with continued stirring and at such a rate that a temperature of 10° C. was not exceeded in the flask.

The mixture was stirred for another 20 minutes in the ice bath and then 50 ml concentrated aqueous hydrochloric acid was added rapidly. The mixture was stirred for about 10 minutes at room temperature. A black precipitate, which formed during the acid addition, was removed by filtration, washed with ethanol, and discarded, leaving a yellow filtrate.

The yellow filtrate was concentrated under reduced pressure with a bath temperature of about 45° C. When the volume was about 75 ml, the liquid was diluted with water to about 200 ml. The warm solution was clarified by filtration over Celite ® diatomaceous earth and then chilled in ice for two hours. A fluffy, crystalline solid (10.5 g) was collected by filtration. The solid was suspended in water (200 ml), and aqueous ammonium hydroxide was added until precipitation appeared to be complete. The somewhat gummy product was collected by filtration, dried superficially in a stream of air and then recrystallized from about 50 ml of isopropanol using charcoal and Celite ® to give a clear filtered solution. The compound crystallized in rod-like needles, mp 93°–95° C., yield 5.0 g, 41% of theory. Another 0.8 g was obtained from the acidic filtrate by precipitation with ammonia and subsequent diethyl ether extraction.

Appexample 19

5,6-Dimethoxy-2-methylbenzotellurazole, $R'=CH_3$, $R^1=R^2=OCH_3$

$C_{10}H_{11}NO_2Te$
mw=304.80

5,6-Dimethoxy-2-methylbenzotellurazolium chloride (Appexample 12) (10 g) was ground with an equal quantity of sodium bicarbonate and a little water in a mortar until evolution of carbon dioxide ceased. The product was collected by filtration, washed with water and dried in a vacuum to yield ≃8.5 g of colorless powder, m.p. 78°–80° C. Slow crystallization from cyclohexane yielded well defined prisms, m.p. 80°–83° C. The mass spectra and nuclear magnetic resonance spectra were in agreement with that expected for the structural formula.

Appexample 20

5-Methoxy-2-methylbenzotellurazole, $R'=CH_3$, $R^1=OCH_3$, $R^2=H$ $C_9H_9NOTe$
mw=274.77

5-Methoxy-2-methylbenzotellurazolium chloride (Appexample 13) (3.7 g=0.012 mole) was suspended in water, sodium bicarbonate in excess of that stoichiometrically required was added, and the free base product was extracted with diethyl ether. After washing with saturated sodium sulfate solution, the organic phase was dried and evaporated under reduced pressure to give a residual oil (3.2 g) which was identified by its nuclear magnetic resonance spectra. C, H, N, O and Te elemental analyses were in agreement with that expected for the structural formula.

Appexample 21

2,5-Dimethylbenzotellurazole, $R'=R^1=CH_3$, $R^2=H$ $C_9H_9NTe$
mw=258.69

2,5-Dimethylbenzotellurazolium chloride (Appexample 14) (3.5 g) was treated in an aqueous suspension with sodium bicarbonate in excess of that stoichiometrically required. The free base product was isolated by extraction with diethyl ether and evaporation to dryness. The residue was recrystallized from ≈50 ml isopropanol to yield 1.7 g colorless needles, m.p. 126°–128° C.

Appexample 22

2,5,6-Trimethylbenzotellurazole, $R'=R^1=R^2=CH_3$ $C_{10}H_{11}NTe$
mw×272.81

2,5,6-Trimethylbenzotellurazolium chloride (Appexample 15) was converted to the free base product by treatment with sodium carbonate (15 g) in water and extraction with dichloromethane (300 ml). The extract was washed as described above, dried, and evaporated to a cream colored crystalline residue (10.45 g), which was recrystallized from isopropanol (50 ml). A yield of faintly yellow needles, m.p. 101°–103° C. was obtained.

Appexample 23

2-Methyl-5-methylthiobenzotellurazole, $R'=CH_3$, $R^1=SCH_3$, $R^2=H$ $C_9H_9NSTe$
mw=290.84

2-Methyl-5-methylthiobenzotellurazolium chloride (Appexample 16) (11.5 g=0.035 mole) was suspended in water and sodium bicarbonate in excess of that stoichiometrically required was added. The free base was extracted into dichloromethane. The organic solution was washed with saturated aqueous sodium sulfate, dried, and evaporated in vacuum to a yellow oil (9.06 g). Upon addition of isopropanol (40 ml) the oil crystallized spontaneously to almost white needles to give 8.18 g, 79.8% of theory, m.p. 64°–67° C.

Appexample 24

5-Hydroxy-2-methylbenzotellurazole, $R'=CH_3$, $R^1=OH$, $R^2=H$ $C_8H_7NOTe$
mw=260.75

5-Hydroxy-2-methylbenzotellurazolium chloride (Appexample 17) (7.45 g) was dissolved in warm water (300 ml) and a slurry of sodium bicarbonate (8 g) in water was added slowly. The free base product separated as a cream colored amorphous solid, which was collected by filtration, washed with water, and dried in a vacuum over Drierite ® brand calcium sulfate drying agent, yield 6.3 g. The material was then recrystallized from isopropanol (50 ml) to give a recovery of ≈4.0 g, m.p. 190°–192° C.

Appexample 25

2-Ethylbenzotellurazole, $R'=C_2H_5$, $R^1=R^2=H$ $C_9H_9NTe$
mw=258.76

2-Phenylazophenyltellurium trichloride (Preparation A) (10.4 g, 0.025 mole) was suspended in ethanol (100 ml) in a flask equipped with a nitrogen gas inlet, magnetic stirrer, reflux condenser, and powder addition funnel. While stirring, unde a nitrogen atmosphere, at room temperature, sodium borohydride (3.8 g, 0.10 mole) was added in increments at a rate sufficient to maintain a vigorous exothermic reaction. Stirring of the reaction mixture at room temperature was continued for 30 minute after the addition was complete, maintaining the nitrogen atmosphere. A thermometer was inserted while still maintaining a nitrogen atmosphere and propionic anhydride (3.9 g, 0.03 mole) was added dropwise. The reaction temperature rose from 25° C. to 30° C. Upon completion of the addition, stirring was continued until the temperature returned to 25° C. Concentrated hydrochloric acid (25 ml) was added dropwise to the reaction mixture, resulting in formation of a black solid. The temperature rose to around 50° C. Stirring was continued until the temperature returned to 25° C. The black solid was removed by filtration, and washed with ethanol, and discarded. The filtrate was concentrated in a rotary evaporator, diluted with about an equal volume of water, filtered through a Celite ® pad, and neutralized to a pH of about 7 with sodium bicarbonate. Extraction with diethyl ether and removal of the ether from the extracts left a red, oily semi-solid, which was purified by being dissolved in dichloromethane and being applied to a thick layer silica gel chromatography plate. An ultraviolet absorbing substance separated as a pale yellow oil. This was determined to be pure by thin layer chromatography. The infrared and nuclear magnetic resonance spectra were in agreement with that expected for the structural formula.

APPEXAMPLES 26–28

Appexamples 26 through 28 illustrate the preparation of naphthotellurazoles.

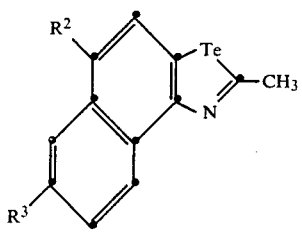

Appexample 26

2-Methylnaphtho[1,2-d]tellurazole, $R^3 = R^2 = H$ $C_{12}H_9NTe$
mw = 294.80

3-Chloronaphth[2,1-c][1,2,5]oxatellurazole (Appexample 2) (48.0 g=0.15 mole) was suspended in a mixture of methanol (150 ml) and tetrahydrofuran (700 ml) in a two liter 3 necked flask fitted with a mechanical stirrer, a condenser, a powder addition funnel, and a nitrogen inlet. The starting compound was reduced by gradual addition of sodium borohydride (14.2 g=0.375 mole) until the reaction mixture was a pale brown. The powder addition funnel was removed and replaced with a stopper. Final addition of sodium borohydride then took place through the condenser until the appearance of the reduced material no longer changed. The mixture was chilled in ice, still under nitrogen, and acetic anhydride (15.3 g=0.15 mole) was added dropwise. The acetylation was permitted to proceed for about 30 minutes. Concentrated hydrochloric acid (75 ml=0.75 mole) was added in one portion. After stirring the mixture, which now contained a black precipitate, for 30 minutes until it reached room temperature, the precipitate was collected by vacuum filtration, rinsed with tetrahydrofuran and air dried.

The solid was then suspended in 350 ml isopropanol, 25 ml concentrated ammonium hydroxide was added, and the mixture was heated to boiling and filtered rapidly with suction. On cooling, needles (18.65 g, 42% of theory) precipitated from the filtrate. For analyses the product was recrystallized once from isopropanol and exhibited m.p. 101°-103° C. Elemental analyses were in agreement with that expected for the structural formula.

Appexample 27

7-Methoxy-2-methylnaphtho[1,2-d]-tellurazole, $R^3 = OCH_3$, $R^2 = H$ $C_{13}H_{11}NOTe$
mw = 324.83

3-Chloro-7-methoxynaphth[2,1,c][1,2,5]oxatellurazole (Appexample 5) (17.45 g=0.05 mole) was reduced, acetylated, and treated with hydrochloric acid using the same method and reagent quantities as given for Appexample 26. Following the procedure described in Appexample 26, there were obtained 4.93 g, 30.2% of theory, silvery fluffy needles (m.p. 120°-123° C.). The elemental analyses were in agreement with that expected for the structural formula.

Appexample 28

2,5-Dimethylnaphtho[1,2-d]tellurazole, $R^3 = H$, $R^2 = CH_3$ $C_{13}H_{11}NTe$ mw = 308.83

3-Chloro-5-methylnaphth[2,1-c][1,2,5]oxatellurazole (Appexample 4) (16.7 g=0.05 mole) was suspended in a mixture of tetrahydrofuran (THF, 200 ml) and methanol (40 ml) in a 500 ml three necked flask fitted with a nitrogen inlet, a condenser, and a powder addition funnel. Sodium borohydride was added under a nitrogen atmosphere and in small portions until the reaction mixture was a pale orange yellow. This required about 5 to 6 g. The powder addition funnel was then removed and replaced with a stopper. The reaction mixture was then cooled to 5° C. and acetic anhydride (5.1 g=0.05 mole) added slowly through the condenser. The reaction mixture transiently turned a bright orange. Concentrated hydrochloric acid (25 ml) was then added in one portion, the ice bath removed, and the mixture stirred to room temperature. As the reaction mixture warmed up, a crystalline deposit appeared and was collected by filtration. The crystalline deposit was washed with tetrahydrofuran until the filtrate was colorless and clear. The filtrate was then heated to boiling with a mixture of isopropanol (175 ml) and concentrated ammonium hydroxide (25 ml) and filtered hot with Celite ®, the cooled filtrate was diluted with water until crystallization started. A first crop of pale yellow needles (5.06 g), m.p. 110°-112° C. was obtained. A further 1.65 g of product were obtained by two further extractions with the same solvent mixture, giving a total yield of 6.71 g=43.3% of theory. For analysis, the material was recrystallized from isopropanol. This did not change the melting point. Elemental analyses were in agreement with that expected for the structural formula.

Appexample 29

2-Methyl-3H-benzotellurazolium Todide

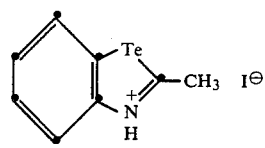

$C_8H_8INTe$
mw = 372.67

To a solution of 2-methylbenzotellurazole (Appexample 18) (0.81 g, 0.0033 mole) in acetone (25 ml), chilled in an ice bath, was added slowly with stirring 55 mole percent hydriodic acid (1 ml). The product began precipitating from solution. After the addition was complete, the mixture was stirred at ice bath temperature for approximately 10 minutes. The solid was isolated by filtration, washed with diethyl ether, and dried under vacuum at room temperature. Yield 1.13 g (92%) of yellow powder, m.p. 209°-211° C. The C, H, and N elemental analyses and the infrared, nuclear magnetic resonance, and mass spectra of the sample were in agreement with that expected for the structural formula.

APPEXAMPLES 30-59

Appexamples 30 through 59 illustrate the preparation of N-alkylated benzotellurazolium salts.

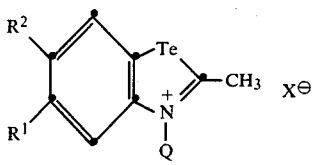

Appexample 30

2,3-Dimethylbenzotellurazolium Trifluoromethanesulfonate, Q=CH$_3$, R$^1$=R$^2$=H, X=CF$_3$SO$_3$ mw=408.85
C$_{10}$H$_{10}$F$_3$NO$_3$STe 2-Methylbenzotellurazole (Appexample 18) (10.5 g, 0.043 mole) was dissolved in dry dichloromethane (75 ml). Freshly distilled methyl trifluoromethanesulfonate (7.5 g, 0.045 mole) was added to the solution. An exothermic reaction occurred immediately. After a few minutes a crystalline product separated which was collected by filtration, washed with diethyl ether, and dried. Yield 16.86 g (96%). The pale yellow powder was dissolved in acetone (100 ml) and reprecipitated by adding diethyl ether to the solution until it became turbid. Colorless plates separated on chilling. Yield 15.33 g (87% of theory); mp 160°-162° C.

Appexample 31

5,6-Dimethoxy-2,3-dimethylbenzotellurazolium Trifluoromethanesulfonate, Q=CH$_3$, R$^1$=R$^2$=OCH$_3$, X=CF$_3$SO$_3$ C$_{12}$H$_{14}$F$_3$NO$_5$STe
mw=468.90

5,6-Dimethoxy-2-methylbenzotellurazole (Appexample 19) (4.8 g=0.013 mole) was dissolved in dichloromethane (75 ml), and methyl trifluoromethanesulfonate (2.48 g=1.66 ml=0.013 mole) was added. The solution turned cloudy and crystals started to deposit within a few minutes. Precipitation was completed by addition of diethyl ether. The product was collected by filtration to give 5.5 g, 86.5% of theory, m.p. 210°-234° C. The product was recrystallized from boiling acetone ($\simeq$130 ml required) m.p. 242°-243° C.

The quaternary ammonium salts prepared in Appexamples 32 through 36 below were all prepared in high yield by combining stoichiometric quantities of the respective base and methyl trifluoromethanesulfonate in dichloromethane, precipitating with diethyl ether, and recrystallization from acetone, with diethyl ether in some instances being added. The C, H, F, N and Te elemental analyses and the nuclear magnetic resonance spectra were consistent with that expected for the structures of each of the quaternary salts.

Appexample 32

5-Methoxy-2,3-dimethylbenzotellurazolium Trifluoromethanesulfonate, Q=CH$_3$, R$^1$=OCH$_3$, R$^2$=H, Q=CH$_3$, X=CF$_3$SO$_3$ C$_{11}$H$_{12}$F$_3$NO$_4$STe
mw=438.87
m.p. 197°-198° C.

Appexample 33

2,3,5-Trimethylbenzotellurazolium Trifluoromethanesulfonate, Q=R$^1$=CH$_3$, R$^2$=H, X=CF$_3$SO$_3$ C$_{11}$H$_{12}$F$_3$NO$_3$STe
mw=422.77
m.p. 215°-217° C.

Appexample 34

2,3,5,6-Tetramethylbenzotellurazolium Trifluoromethanesulfonate,

Q=R$^1$=R$^2$=CH$_3$, X=CF$_3$SO$_3$
C$_{12}$H$_{14}$F$_3$NO$_3$STe
mw=436.91
m.p. 230°-233° C.

Appexample 35

2,3-Dimethyl-5-methylthiobenzotellurazolium Trifluoromethanesulfonate, Q=CH$_3$, R$^1$=SCH$_3$, R$^2$=H, X=CF$_3$SO$_3$ C$_{11}$H$_{12}$F$_3$NO$_3$S$_2$Te
mw=454.94
m.p. 195°-195° C.

Appexample 36

5-Hydroxy-2,3-dimethylbenzotellurazolium Trifluoromethanesulfonate, Q=CH$_3$, R$^1$=OH, R$^2$=H, X=CF$_3$SO$_3$ C$_{10}$H$_{10}$F$_3$NO$_4$STe
mw=434.85
m.p. 171°-175° C.

Appexample 37

3-Ethyl-5,6-dimethoxy-2-methylbenzotellurazolium Trifluoromethanesulfonate, Q=C$_2$H$_5$, R$^1$=R$^2$=OCH$_3$, X=CF$_3$SO$_3$ C$_{13}$H$_{16}$F$_3$NO$_5$STe
mw=482.93 (15.7 g, 0.005 mole).

5,6-Dimethoxy-2-methylbenzotellurazole (Appexample 19) was dissolved in chloroform (150 ml). A stoichiometric amount of ethyl trifluoromethanesulfonate was added, and the solution was refluxed for two hours under a condenser protected with a drying tube. After cooling the solution was poured slowly into cold diethyl ether (700 ml) with rapid stirring. The product crystallized and was collected by filtration. Yield 19.3 g (77.3% of theory).

The quaternary salts of the next three examples were obtained in the same general way as that of Appexample 37, except as noted, using the appropriate benzotellurazole.

Appexample 38

3-Ethyl-5-methoxy-2-methylbenzotellurazolium Trifluoromethanesulfonate, Q=C$_2$H$_5$, R$^1$=OCH$_3$, R$^2$=H, X=CF$_3$SO$_3$ C$_{12}$H$_{14}$F$_3$NO$_4$STe
mw=452.90

The alkylation was carried out in diethyl ether at room temperature. Several crops of crystalline product were collected over three days. Total yield 15.0 g (73% of theory).

Appexample 39

3-Ethyl-2,5,6-trimethylbenzotellurazolium Trifluoromethanesulfonate, $Q=C_2H_5$, $R^1=R^2=CH_3$, $X=CF_3SO_3$ $C_{13}H_{16}F_3NO_3STe$ mw=450.93.

The product precipitated directly from chloroform. Yield 16.6 g (91% of theory).

Appexample 40

3-Ethyl-2-methyl-5-methylthiobenzotellurazolium Trifluoromethanesulsulfonate, $Q=C_2H_5$, $R^1=SCH_3$, $R^2=H$, $X=CF_3SO_3^\theta$ $C_{12}H_{14}F_3NO_3S_2Te$ mw=468.96.

The product separated from chloroform to which diethyl ether was added to aid precipitation. A gummy residue was recrystallized from ethanol.

APPEXAMPLES 41–44

Appexamples 41 through 44 use 2-propen-1-yl trifluoromethanesulfonate in a dry solution of carbon tetrachloride. This was prepared by dissolving trifluoromethanesulfonic anhydride in carbon tetrachloride (about 10 ml of solvent per g of anhydride) and chilling the solution to near 0° C. Under a nitrogen atmosphere a solution of equimolar amounts of 2-propen-1-ol (allyl alcohol) and pyridine in carbon tetrachloride (about 5 ml of solvent per g of anhydride) was added dropwise to the chilled anhydride solution. Stirring was continued for about 30 minutes after the addition was complete, maintaining the nitrogen atmosphere and ice-bath temperature. The reaction mixture was then filtered through a pad of sodium sulfate, and the dried solution was used in the subsequent examples.

Appexample 41

A. 2-Methyl-3-(2-propen-1-yl)benzotellurazolium Trifluoromethanesulfonate, $Q=CH_2-CH=CH_2$ $R^1=R^2=H$, $X=CF_3SO_3$ $C_{12}H_{12}F_3NO_3STe$ mw=434.90.

The dried solution of 2-propen-1-yl trifluoromethanesulfonate (0.008 mole) in carbon tetrachloride was placed in a dropping funnel and added to a solution of 2-methylbenzotellurazole (Appexample 18) (1.62 g, 0.0066 mole) in dichloromethane (25 ml) under a nitrogen atmosphere at room temperature. After the addition was complete, stirring was continued for 18 hours. The solid was isolated by filtration, washed with diethyl ether, and dried at room temperature under vacuum. Yield 0.43 g (15%), m.p. 90°–93° C. Infrared, nuclear magnetic resonance, and mass spectra were in agreement with that expected for the structural formula.

B. 2-Methyl-3-(2-propen-1-yl)benzotellurazolium Iodide, $Q=CH_2-CH=CH_2$, $R^1=R^2=H$, $X=I$ $C_{11}H_{12}INTe$ mw=412.73.

The solvents from the filtrates above were removed under vacuum and the dark orange semisolid redissolved in acetone (about 30 ml). The solution was stirred, chilled, and treated with a saturated solution of sodium iodide in acetone (about 5 ml). The solid was isolated by filtration, washed with acetone, diethyl ether, and dried. Yield 0.52 g (21% of theory) m.p. 205°–207° C. Elemental analyses and nuclear magnetic resonance spectra were in agreement with that expected for the structural formula.

Appexample 42

5,6-Dimethoxy-2-methyl-3-(2-propen-1-yl)benzotellurazolium Trifluoromethanesulfonate, $Q=CH_2-CH=CH_2 R^1=R^2=OCH_3$, $X=CF_3SO_3$ $C_{14}H_{16}F_3NO_5STe$ mw=494.95.

A dried solution of 2-propen-1-yl tri-fluoromethanesulfonate (0.002 mole) in carbon tetrachloride was added dropwise to a solution of 5,6-dimethoxy-2-methylbenzotellurazole (Appexample 19) (0.50 g, 0.0016 mole) in dichloromethane (25 ml) under a nitrogen atmosphere at room temperature. After the addition was complete, stirring was continued for 7 hours. The solid was isolated by filtration, washed with diethyl ether, and dried at room temperature under vacuum. Yield 0.38 g. A mass spectrogram of the compound was in agreement with that expected for the structural formula.

Appexample 43

5-Methoxy-2-methyl-3-(2-propen-1-yl)benzotellurazolium Trifluoromethanesulfonate, $Q=CH_2CH=CH_2$, $R^1=OCH_3$, $R^2=H$, $X=CF_3SO_3$ $C_{13}H_{14}F_3NO_4STe$ mw=464.92.

5-Methoxy-2-methylbenzotellurazole (Appexample 20) (0.91 g, 0.033 mole), dissolved in dichloromethane (25 ml), was added at room temperature under a nitrogen atmosphere to the solution of 2-propen-1-yl trifluoromethanesulfonate (0.004 mole) from a dropping funnel. The mixture was stirred at room temperature for another 21 hours after the addition was complete, maintaining the nitrogen atmosphere. The solid was isolated by filtration, washed with diethyl ether, and dried at room temperature under vacuum. Yield 0.90 g.

Appexample 44

2,5,6-Trimethyl-3-(2-propen-1-yl)benzotellurazolium Trifluoromethanesulfonate, $Q=CH_2CH=CH_2$, $R^1=R^2=CH_3$, $X=CF_3SO_3$ $C_{14}H_{16}F_3NO_3STe$ mw=462.94.

To a solution of 2,5,6-trimethylbenzotellurazole (Appexample 22) (9.90 g, 0.0033 mole) in dichloromethane (30 ml) was added the solution of 2-propen-1-yl trifluoromethanesulfonate (0.004 mole) rapidly at room temperature under a nitrogen atmosphere, with good stirring. Solid began separating 10 minutes after the addition was complete. Stirring under a nitrogen atmosphere was continued for about 18 hours. The solid was isolated by filtration, washed with diethyl ether, and dried under vacuum at room temperature. Yield 1.0 g, m.p. 162°–164° C. The mass spectra agreed with the assigned structural formula.

APPEXAMPLES 45–48

2-Propyn-1-yl trifluoromethanesulfonate was prepared in carbon tetrachloride solution and used as a dried solution in Appexamples 45 through 48 in the same way that 2-propen-1-yl trifluoromethanesulfonate was prepared and was used in Appexamples 41 through 44 starting with 2-propyn-1-ol (propargyl alcohol) and trifluoromethanesulfonic anhydride.

Appexample 45

2-Methyl-3-(2-propyn-1-yl)benzotellurazolium Trifluoromethanesulfonate, Q=CH$_2$C≡CH, R$^1$=R$^2$=H, X=CF$_3$SO$_3$ C$_{12}$H$_{10}$F$_3$NO$_3$STe
mw=432.87.

2-Methylbenzotellurazole (Appexample 18) (0.81 g, 0.0033 mole) was dissolved in dichloromethane (30 ml). A solution in carbon tetrachloride (25 ml) of 2-propyn-1-yl trifluoromethanesulfonate, prepared as described above, (0.004 mole) was placed in a dropping funnel and added at room temperature under a nitrogen atmosphere to the benzotellurazole solution. The mixture was stirred for about 20 hours after the addition was complete, forming a white solid, which was isolated by filtration, washed with dichloromethane, and dried at room temperature under vaccum. Yield 0.60 g (42% of theory), m.p. 150°-152° C. The infrared, nuclear magnetic resonance and mass spectra were consistent with the structural formula.

Appexample 46

5,6-Dimethoxy-2-methyl-3-(2-propyn-1-yl)benzotellurazolium Trifluoromethanesulfonate,
Q=CH$_2$—C≡CH, R$^1$=R$^2$=OCH$_3$, X=CF$_3$SO$_3$ C$_{14}$H$_{14}$F$_3$NO$_5$STe
mw=492.92.

5,6-Dimethoxy-2-methylbenzotellurazole (Appexample 19) (1.0 g, 0.033 mole) was dissolved in dichloromethane (25 ml). The solution of 2-propynl-1-yl trifluoromethanesulfonate, prepared as described above, was added from a dropping funnel under a nitrogen atmosphere. After completion of the addition the mixture was stirred for 16 hours at room temperature. The solid was isolated by filtration, washed with diethyl ether, and dried under vacuum at room temperature. Yield, 1.14 g (70% of theory). The infrared, nuclear magnetic resonance, and mass spectra were in agreement with that expected for the structural formula.

Appexample 47

5-Methoxy-2-methyl-3-(2-propyn-1-yl)benzotellurazolium Trifluoromethanesulfonate,
Q=CH$_2$C≡CH, R$^1$=OCH$_3$, R$^2$=H, X=CF$_3$SO$_3$ C$_{13}$H$_{12}$F$_3$NO$_4$STe
mw=462.89.

This compound was prepared in the same way and on the same scale as the compound of Appexample 46, except that 5-methoxy-2-methylbenzotellurazole (Appexample 20) was used in place of the 5,6-dimethoxy-2-methylbenzotellurazole. Yield 1.23 g, 80% of theory, pale tan powder, m.p. 172°-174° C. (dec). The infrared, nuclear magnetic resonance, and mass spectra were in agreement with that expected for the structural formula.

Appexample 48

2,5,6-Trimethyl-3-(2-propyn-1-yl)benzotellurazolium Trifluoromethanesulfonate, Q=CH$_2$C≡CH, R$^1$=R$^2$=CH$_3$, X=CF$_3$SO$_3$ C$_{14}$H$_{14}$F$_3$NO$_3$STe
mw=460.93.

This compound was prepared in the same way and on the same molar scale as the compound of Appexample 46, except that 2,5,6-trimethylbenzotellurazole (Appexample 22) was used in place of 5,6-dimethoxy-2-methylbenzotellurazole. Yield 1.10 g (72% of theory) cream colored powder, m.p. 189°-192° C. dec. The infrared, nuclear magnetic resonance, and mass spectra were in agreement with that expected for the structural formula.

APPEXAMPLES 49-52

Ethoxycarbonylmethyl trifluoromethanesulfonate was prepared in carbon tetrachloride solution and used as a dried solution in Appexamples 49 through 52 in the same way that 2-propen-1-yl trifluoromethanesulfonate was prepared and used in Appexamples 41 through 44, starting with hydroxyacetic acid, ethyl ester (ethyl glycolate).

Appexample 49

3-Ethoxycarbonylmethyl-2-methylbenzotellurazolium Trifluoromethanesulfonate

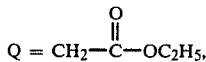

R$^1$ = R$^2$ = H, X = CF$_3$SO$_3$

C$_{13}$H$_{14}$F$_3$NO$_5$STe
mw=480.91.

2-Methylbenzotellurazole (Appexample 18) (0.81 g, 0.0033 mole) was dissolved in dichloromethane (30 ml). The solution of ethoxycarbonylmethyl trifluoromethanesulfonate (0.004 mole) in carbon tetrachloride prepared as described above, was placed in a dropping funnel and added to the benzotellurazole solution at room temperature under a nitrogen atmosphere. After the addition was complete, the mixture was stirred at room temperature, while maintaining a nitrogen atmosphere for 22 hours. The solid was isolated by filtration and dried at room temperature under vacuum. Yield was 0.62 g (39% of theory) of a white powder, m.p. 156°-158° C. The C, H, N and S elemental analyses and the infrared, nuclear magnetic resonance, and mass spectra were all in agreement with that expected for the structural formula.

Appexample 50

3-Ethoxycarbonylmethyl-5,6-dimethoxy-2-methylbenzotellurazolium Iodide

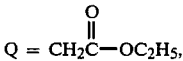

R$^1$ = R$^2$ = OCH$_3$, X = I

C$_{14}$H$_{18}$INO$_4$Te
mw=518.81.

5,6-Dimethoxy-2-methylbenzotellurazole (Appexample 19) (1.22 g, 0.004 mole) was dissolved in dichloromethane (25 ml). The solution of ethoxycarbonylmethyl trifluoromethanesulfonate (0.004 mole) in carbon tetrachloride, which was prepared as described above, was placed in a dropping funnel and added slowly at room temperature and under a nitrogen atmosphere to the benzotellurazole solution. The reaction mixture was filtered to remove the small amount of solid that had formed. The solvents were removed from the filtrate under reduced pressure, and the residue was redissolved in acetone. The solution was treated with saturated sodium iodide in acetone. This was stirred for 15 minutes. After crystallization began, the mixture was chilled and then filtered. The solid was washed with diethyl ether and dried at room temperature under a vacuum. Yield 0.45 g (22% of theory) of pale yellow crystals, m.p. 184°–186° C. The infrared, nuclear magnetic resonance, and mass spectra were in agreement with that expected for the structural formula.

Appexample 51

Ethoxycarbonylmethyl-5-methoxy-2-methyl-3-benzotellurazolium Iodide $Q = CH_2\underset{\underset{O}{\|}}{C}OC_2H_5$, $R^1 = OCH_3$, $R^2 = H$, $X = I$ $C_{13}H_{16}INO_3Te$ This compound was prepared in the same way and on the same scale as the compound of Appexample 50, except that 5-methoxy-2-methylbenzotellurazole (Appexample 20) was used in place of 5,6-dimethoxy-2-methylbenzotellurazole. Yield 0.45 g (28% of theory) of a greenish yellow powder, m.p. 215°–217° C. (dec). The infrared, nuclear magnetic resonance, and mass spectra were in agreement with that expected for the structural formula.

Appexample 52

3-Ethoxycarbonylmethyl-2,5,6-trimethylbenzotellurazolium Trifluoromethanesulfonate $Q = CH_2-\underset{\underset{O}{\|}}{C}-OC_2H_5$, $R^1 = R^2 = CH_3$, $X = CF_3SO_3$ $C_{15}H_{18}F_3NO_5STe$
mw=508.96.

2,5,6-Trimethylbenzotellurazole (Appexample 22) (0.90 g, 0.0033 mole) was dissolved in dichloromethane (25 ml). A solution of ethoxycarbonylmethyl trifluoromethanesulfonate was placed in a dropping funnel and added rapidly to the benzotellurazole solution, at room temperature and under a nitrogen atmosphere. Stirring was continued for 20 hours after the addition was complete at room temperature while maintaining a nitrogen atmosphere. The solid was isolated by filtration, washed with diethyl ether, and dried at room temperature under vacuum. Yield 0.83 g (49% of theory) of gray-white powder, m.p. 177°–179° C. (dec). The infrared, nuclear magnetic resonance, and mass spectra were in agreement with that expected for the structural formula.

An additional quantity of the compound as the iodide salt was obtained by removing the solvents from the filtrate under reduced pressure, redissolving the residue in acetone, and treating with a saturated solution of sodium iodide in acetone. The yellow solid which formed was isolated by filtration, washed, and dried as before. Yield 0.30 g, m.p. 222°–224° (dec.). The various spectra were also in agreement with that expected for the structural formula.

APPEXAMPLES 53–55

Benzyl trifluoromethanesulfonate was prepared in carbon tetrachloride solution and used as a dried solution in Appexamples 53 through 55, in the same way the 2-propen-1-yl trifluoromethanesulfonate was prepared and used in Appexamples 41 through 44, starting with benzyl alcohol and trifluoromethanesulfonic anhydride.

Appexample 53

3-Benzyl-2-methylbenzotellurazolium Trifluoromethanesulfonate $Q = CH_2-$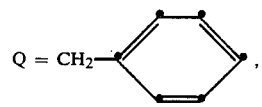, $R^1 = R^2 = H$, $X = CF_3SO_3$ $C_{16}H_{14}F_3NO_3STe$
mw=484.94.

2-Methylbenzotellurazole (Appexample 18) (0.81 g, 0.0033 mole) was dissolved in dichloromethane (25 ml). The solution of benzyl trifluoromethanesulfonate (0.004 mole) in carbon tetrachloride, prepared as described above, was placed in a dropping funnel and added at room temperature under a nitrogen atmosphere to the benzotellurazole solution. Stirring was continued for 18 hours at room temperature after the addition was complete, maintaining a nitrogen atmosphere. The solid was isolated by filtration, washed with diethyl ether, and dried at room temperature under a vacuum. Yield 0.30 g (19% of theory) of a white powder, m.p. 120°–122° C. The infrared, nuclear magnetic resonance, and mass spectra of this compound were in agreement with that expected for the structural formula.

Appexample 54

3-Benzyl-5,6-dimethoxy-2-methylbenzotellurazolium Trifluoromethanesulfonate $Q = CH_2-$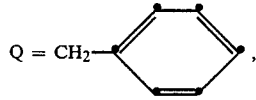, $R^1 = R^2 = OCH_3$, $X = CF_3SO_3$ $C_{18}H_{18}F_3NO_5STe$
mw=544.99.

This compound was prepared in the same way and on the same scale as the compound of Appexample 53, except that 5,6-dimethoxy-2-methylbenzotellurazole (Appexample 19) was used in place of 2-methylbenzotellurazole. Yield 0.50 g of a pale gray powder, m.p. 179°–182° C. (dec). The infrared, nuclear magnetic resonance, and mass spectra were in agreement with that expected for a mixture of desired compound and the hydro salt 5,6-dimethoxy-2-methylbenzotellurazole.

Appexample 55

3-Benzyl-2,5,6-trimethylbenzotellurazolium Iodide

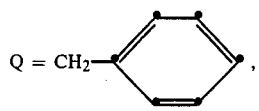

$R^1 = R^2 - CH_3$, $X = I$ $C_{17}H_{18}INTe$
mw=490.84.

This compound was prepared in the same way and on the same scale as the compound of Appexample 53, except that 2,5,6-trimethylbenzotellurazole (Appexample 22) was used in place of 2-methylbenzotellurazole and the product which was isolated directly from the reaction mixture was primarily the hydro salt of 2,5,6-tri-methylbenzotellurazole. The solvents were removed from the filtrate under reduced pressure. The residue was redissolved in acetone and treated with a saturated solution of sodium iodide in acetone. The solid isolated was washed and dried as before. Yield 0.10 g, m.p. 203°–206° C. (dec). The infrared and nuclear magnetic resonance spectra were in agreement with that expected for the structural formula.

Appexample 56

2-Methyl-3-[2-(2,2-dimethyl-1,3-dioxolan-4-yl)ethyl]-benzotellurazolium Iodide

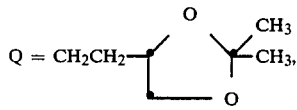

$R^1 = R^2 = H$, $X = I$ $C_{15}H_{20}INO_2Te$
mw=500.84.

2-(2,2-Dimethyl-1,3-dioxolan-4-yl)ethyl trifluoromethane sulfonate was prepared in carbon tetrachloride solution and used as a dried solution in this example in the same way as 2-propen-1-yl trifluoromethanesulfonate was prepared and used in Appexamples 41 through 44, starting with 2,2dimethyl-4-(2-hydroxyethyl)1,3-dioxolane and trifluoromethanesulfonate.

2-Methylbenzotellurazole (Appexample 18) (0.81 g, 0.0033 mole) was dissolved in dichloromethane (20 ml), and a solution of 2-(2,2-dimethyl-1,3-dioxolan-4-yl)ethyl trifluoromethanesulfonate in carbon tetrachloride was added from a dropping funnel at room temperature under a nitrogen atmosphere. After the addition was complete, the mixture was stirred for 21 hours at room temperature while maintaining a nitrogen atmosphere. The reaction mixture was filtered, and the solvent was removed from the filtrate under reduced pressure. The residue was dissolved in a small amount of acetone, and the solution was then treated with a saturated solution of sodium iodide in acetone. Diethyl ether was added to precipitate the product, which was isolated by filtration, washed with diethyl ether, and dried at room temperature under vacuum. The yield of pale yellow powder was 0.67 g (41% of theory), m.p. 158°–160° C. C, H and N elemental analyses and the infrared, nuclear magnetic resonance, and mass spectra of this sample were in agreement with that expected for the structural formula.

APPEXAMPLES 57–59

The following three compounds, Appexamples 57 through 59, were prepared by the same general procedure. The appropriate 2-methylbenzotellurazole base, 2-methylbenzotellurazole for Appexample 57, 5,6-dimethoxy-2-methylbenzotellurazole for Appexample 58, and 5-methoxy-2-methylbenzotellurazole for Appexample 59, was heated with trimethylene sulfate in equimolar amounts at 75° to 80° in a flask equipped with a magnetic stirrer and reflux condenser for 18 hours (3 hours in Appexample 59). The reactants initially formed a melt, but ultimately the mass became solid. After cooling to room temperature the solid was removed and then crushed and stirred in acetone until a uniform slurry was obtained. The solid was isolated by filtration, washed with more acetone and dried at room temperature under a vacuum. At least one product, Appexample 59, was observed to decompose on standing in air. Infrared, nuclear magnetic resonance, and mass spectra of each of these three examples were in agreement with that expected for the structural formulae.

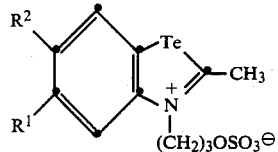

Appexample 57

Anhydro-2-methyl-3-(3-sulfatopropyl)benzotellurazolium Hydroxide, $R^1 = R^2 = H$ $C_{11}H_{13}NO_4STe$
mw=382.88.

Yield 79%, tan powder, m.p. 202°–204° C. (dec.).

Appexample 58

Anhydro-5,6-dimethoxy-2-methyl-3-(3-sulfatopropyl)-benzotellurrazolium Hydroxide, $R^1 = R^2 = OCH_3$ $_{13}H_{17}NO_6STe$
mw=442.93.

Yield 61%, tan powder, m.p. >250° C.

Appexample 59

Anhydro-5-methoxy-2-methyl-3-(3-sulfatopropyl)benzothiazolium Hydroxide, $R^1 = OCH_3$, $R^2 = H$ $C_{12}H_{15}NO_5STe$
mw=412.91.

Yield 79%, tan powder.

APPEXAMPLES 60–62

Appexamples 60 through 62 illustrate the preparation of the 3-substituted naphtho[1,2-d]tellurazolium salts:

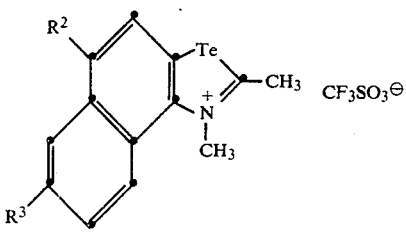

Appexample 60

1,2-Dimethylnaphtho[1,2-d]tellurazolium Trifluoromethanesulfonate, $R^3=R^2=H$ $C_{14}H_{12}F_3NO_3STe$
mw=458.92.

2-Methylnaphtho[1,2-d]tellurazole (Appexample 26) (14.8 g=0.05 mole) was dissolved in dry dichloromethane, and methyl trifluoromethanesulfonate (5.52 ml=0.05 mole) was added. The flask was sealed and kept over a weekend. Pale yellow plates (16.1 g, b 70% of theory) formed. The product was recrystallized from 150 ml of acetone by addition of diethyl ether (m.p. 178°-183° C.). The mass and nuclear magnetic resonance spectra were in agreement with that expected for the structural formula.

Appexample 61

7-Methoxy-1,2-dimethylnaphtho[1,2-d]tellurazolium Trifluoromethanesulfonate, $R^3=OCH_3$, $R^2=H$ $C_{15}H_{14}F_3NO_4STe$
mw=488.93.

7-Methoxy-2-methylnaphtho[1,2-d]tellurazole (Appexample 27) (0.98 g=0.03 mole) was alkylated as described above for Appexample 60. The reaction mixture was kept at room temperature for 5 days to yield 0.68 g, 46% of theory, yellow fluffy needles (m.p. 174°-183° C.). The mass and nuclear magnetic resonance spectra were in agreement with that expected for the structural formula.

Appexample 62

1,2,5-Trimethylnaphtho[1,2-d]tellurazolium Trifluoromethanesulfonate, $R^3=H$, $R^2=CH_3$ $C_{15}H_{14}F_3NO_3STe$
mw=472.93

2,5-Dimethylnaphtho[1,2-d]tellurazole (Appexample 28) (0.93 g=0.003 mole) was dissolved in dry dichloromethane, and methyl trifluoromethanesulfonate (0.33 ml=0.003 mole) was added. The flask was sealed and kept over a weekend. Bright yellow plates (0.88 g, 61% of theory) formed. The product was recrystallized from 10 ml of acetone by addition of 20 ml of diethyl ether. The melting point was 224°-230° C. The mass and nuclear magnetic resonance spectra were in agreement with that expected for the structural formula.

This invention has been described in detail with reference to preferred embodiments thereof, but it will be understood that variations and modifications can be effected within the spirit and scope of the invention.

What is claimed is:

1. A photographic element containing a radiation sensitive silver halide emulsion and an effective amount of a fog inhibiting agent comprised of a divalent tellurium atom directly linked to a first carbocyclic aromatic nucleus and linked to a second carbocyclic aromatic nucleus through at least one divalent middle chalcogen atom characterized in that said first aromatic nucleus includes an amido ring sustituent.

2. A photographic element according to claim 1 further characterized in that said silver halide emulsion contains surface latent image forming silver halide grains.

3. A photographic element according to claim 2 further characterized in that said silver halide grains are surface chemically sensitized.

4. A photographic element according to claim 2 further characterized in that said silver halide grains are spectrally sensitized.

5. A photographic element according to claim 1 further characterized in that said divalent tellurium atom is directly linked to a middle chalcogen atom which is directly linked to said second aromatic nucleus.

6. A photographic element according to claim 1 further characterized in that said fog inhibiting agent is incorporated in said silver halide emulsion.

7. A photographic element according to claim 6 further characterized in that said fog inhibiting agent is present in a concentration of from 0.005 to 1.0 millimole per silver mole.

8. A photographic element according to claim 7 further characterized in that said fog inhibiting agent is present in a concentration of from 0.5 to 0.01 millimole per silver mole.

9. A photographic element according to claim 1 further characterized in that said fog inhibiting agent satisfies the formula

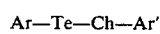

wherein
Ar is an amido substituted first carbocyclic aromatic nucleus;
Ar' is a second carbocyclic aromatic nucleus; and
Ch is one or more middle chalogen atoms chosen from the class consisting of sulfur, selenium, and tellurium.

10. A photographic element according to claim 9 further characterized in that Ch represents a tellurium atom.

11. A photographic element according to claim 10 further characterized in said first and second aromatic nuclei are phenyl nuclei.

12. A photographic element according to claim 11 further characterized in that said phenyl nuclei are amido substituted at a ring carbon atom ortho or para to said tellurium atoms.

13. A photographic element according to claim 12 further characterized in that said phenyl nuclei are amido substituted at a ring carbon atom ortho to said tellurium atoms.

14. A process of producing a photographic image comprising processing a photographic element containing at least one imagewise exposed silver halide emulsion in the presence of a fog inhibiting agent comprised of a divalent tellurium atom directly linked to a first carbocyclic aromatic nucleus and linked to a second carbocyclic aromatic nucleus through at least one divalent middle chalcogen atom characterized in that said first aromatic nucleus includes an amido ring substituent.

15. A process of producing a photographic image according to claim 14 further characterized in that said fog inhibiting agent is initially present in a processing solution in a concentration of from 0.05 to 0.5 millimole per liter.

* * * * *